(12) United States Patent
Lev

(10) Patent No.: US 11,611,848 B2
(45) Date of Patent: Mar. 21, 2023

(54) VERIFYING A PATH OF A MOBILE WIRELESS DEVICE BASED ON WIRELESS MAPPING

(71) Applicant: NEC Corporation Of America, Herzlia (IL)

(72) Inventor: Tsvi Lev, Tel-Aviv (IL)

(73) Assignee: NEC Corporation Of America, Herzlia (IL)

( * ) Notice: Subject to any disclaimer, the term of this patent is extended or adjusted under 35 U.S.C. 154(b) by 336 days.

(21) Appl. No.: 16/904,625

(22) Filed: Jun. 18, 2020

(65) Prior Publication Data

US 2021/0400436 A1 Dec. 23, 2021

(51) Int. Cl.
*H04W 4/029* (2018.01)
*A61L 2/24* (2006.01)
*A61L 2/10* (2006.01)
*H04W 12/037* (2021.01)
*H04W 12/069* (2021.01)
*A61L 2/26* (2006.01)

(52) U.S. Cl.
CPC ............ *H04W 4/029* (2018.02); *A61L 2/10* (2013.01); *A61L 2/24* (2013.01); *A61L 2/26* (2013.01); *H04W 12/037* (2021.01); *H04W 12/069* (2021.01); *A61L 2202/11* (2013.01); *A61L 2202/14* (2013.01); *A61L 2202/16* (2013.01)

(58) Field of Classification Search
CPC . H04W 4/029; H04W 12/037; H04W 12/069; A61L 2/10; A61L 2/24; A61L 2/26; A61L 2202/11; A61L 2202/14; A61L 2202/16
See application file for complete search history.

(56) References Cited

U.S. PATENT DOCUMENTS 10,510,197 B2 * 12/2019 Baumgarte ........ G07C 9/00309
2021/0112064 A1 * 4/2021 Losseva ................ H04L 63/102
2021/0400483 A1 12/2021 Lev

FOREIGN PATENT DOCUMENTS

CN 106447870 A * 2/2017

* cited by examiner

*Primary Examiner* — David E Smith

(57) ABSTRACT

Provided herein are methods and systems for verifying a path in a monitored space, comprising transmitting a device identification (ID) of the mobile wireless device while the mobile wireless device moves through a monitored space, receiving one or more location certificates transmitted, in response to reception of the device ID, by one or more wireless transceivers deployed at a predefined location in the monitored space and having a limited transmission range, each location certificate comprising at least the device ID and a transceiver ID of the respective wireless transceiver, storing the one or more location certificates, and transmitting the one or more location certificates to one or more verification units configured to verify a path of the mobile wireless device in the monitored space estimated according to the predefined location of the one or more wireless transceivers identified by the transceiver ID extracted from the one or more location certificates.

20 Claims, 5 Drawing Sheets

VERIFYING A PATH OF A MOBILE WIRELESS DEVICE BASED ON WIRELESS MAPPING

FIELD AND BACKGROUND OF THE INVENTION

The present invention, in some embodiments thereof, relates to verifying a path of a mobile wireless device, and, more specifically, but not exclusively, to verifying a path of a mobile wireless device in a monitored space based on wireless mapping of the mobile wireless device by wireless devices deployed in predefined locations in the monitored space.

Authenticating and validating users prior to granting them access to restricted areas and/or restricted resources (e.g. terminals, networks, etc.) may be highly desirable for a plurality of applications, systems and/or infrastructures.

While users may be authenticated in a plurality of methods and techniques as known in the art, authenticating users based on their physical location and/or travel paths may provide high benefit in particular in sensitive public locations, for example, office areas, buildings, facilities, schools, hospitals, sports stadiums, train stations, airports and/or the like in which the travel path of people may be highly indicative of their covert intentions.

Moreover, the path tracking may be further applied for tracking disinfection apparatuses manually and/or automatically operated to disinfect public space, and more so in times of epidemic outbreaks such as the outbreak of the COVID-19 epidemic when frequent and efficient disinfection and sanitization must be practiced.

SUMMARY OF THE INVENTION

According to a first aspect of the present invention there is provided a computer implemented method of verifying a path in a monitored space, comprising using one or more processors of a mobile wireless device for:

Transmitting a device identification (ID) of the mobile wireless device while the mobile wireless device moves through a monitored space.

Receiving one or more location certificates transmitted, in response to reception of the device ID, by one or more wireless transceivers deployed at a predefined location in the monitored space and having a limited transmission range. Each location certificate comprising at least the device ID and a transceiver ID of the respective wireless transceiver.

Storing the one or more location certificates.

Transmitting the one or more location certificates to one or more verification units configured to verify a path of the mobile wireless device in the monitored space estimated according to the predefined location of the one or more wireless transceivers identified by their transceiver ID extracted from the one or more location certificates.

According to a second aspect of the present invention there is provided a mobile wireless device for verifying a path in a monitored space, comprising one or more processors executing a code, the code comprising:

Code instructions to transmit a device identification (ID) of the mobile wireless device while the mobile wireless device moves through a monitored space.

Code instructions to receive one or more location certificates transmitted, in response to reception of the device ID, by one or more wireless transceivers deployed at a predefined location in the monitored space and having a limited transmission range. Each location certificate comprising at least the device ID and a transceiver ID of the respective wireless transceiver.

Code instructions to store the one or more location certificates.

Code instructions to transmit the one or more location certificates to one or more verification units configured to verify a path of the mobile wireless device in the monitored space estimated according to the predefined location of the one or more wireless transceivers identified by their transceiver ID extracted from the one or more location certificates.

According to a third aspect of the present invention there is provided a computer implemented method of verifying a path in a monitored space, comprising using one or more processors for:

Receiving one or more location certificates from one or more wireless receivers deployed at a predefined location in the monitored space and having a limited reception range. Each location certificate comprising at least a device identification (ID) of a mobile wireless device detected by one of the wireless receivers and a receiver ID of the respective wireless receiver.

Extracting the device ID and the receiver ID from each of the one or more location certificates.

Estimating a path of the mobile wireless device in the monitored space according to the predefined location of the one or more wireless receivers identified by their receiver ID.

Verifying the estimated path with one or more approved paths based on comparison with one or more approved path.

According to a fourth aspect of the present invention there is provided a system for verifying a path in a monitored space, comprising one or more processors executing a code, the code comprising:

Code instructions to receive one or more location certificates from one or more wireless receivers deployed at a predefined location in the monitored space and having a limited reception range. Each location certificate comprising at least a device identification (ID) of a mobile wireless device detected by one of the wireless receivers and a receiver ID of the respective wireless receiver.

Code instructions to extract the device ID and the receiver ID from each of the one or more location certificates;

Code instructions to estimate a path of the mobile wireless device in the monitored space according to the predefined location of the one or more wireless receivers identified by their receiver ID.

Code instructions to verify the estimated path with one or more approved paths based on comparison with one or more approved path.

In a further implementation form of the first, second, third and/or fourth aspects, the mobile wireless device is associated with a user verified based on his path through the monitored space.

In a further implementation form of the first and/or second aspects, the mobile wireless device is associated with a disinfection apparatus configured to disinfect one or more surfaces in the monitored space. The path of the associated disinfection apparatus is verified with respect to one or more predefined path. The one or more wireless transceivers are deployed in association with the one or more surfaces.

In a further implementation form of the first and/or second aspects, the disinfection apparatus is configured to project Ultra Violet (UV) light to disinfect the one or more surfaces in the monitored space. The verification of the path of the disinfection apparatus further comprising verifying a predefined projection time of the UV light on the one or more surfaces which is sufficient for effectively disinfecting the respective surfaces.

In an optional implementation form of the first and/or second aspects, the disinfection apparatus is configured to project Ultra Violet (UV) light to disinfect the one or more surfaces in the monitored space. The verification of the path of the disinfection apparatus further comprising verifying a predefined projection time of the UV light on the one or more surfaces which is sufficient for effectively disinfecting the respective surfaces.

In an optional implementation form of the first and/or second aspects, the one or more predefined paths are derived from an estimated path in the monitored space which is determined for one or more mobile device associated with a respective user such that the disinfection apparatus is verified to follow the path of the respective users.

In a further implementation form of the first and/or second aspects, the estimated path is verified based on comparison with one or more approved paths.

In a further implementation form of the first and/or second aspects, the limited transmission range defines a limited space in the monitored space in proximity to the one or more wireless transceiver such that only when located within the limited space the mobile wireless device receives the one or more location certificates transmitted by the one or more wireless transceivers.

In a further implementation form of the first and/or second aspects, the device ID is transmitted periodically and/or continuously.

In an optional implementation form of the first and/or second aspects, one or more of the location certificates are encrypted using one or more cryptographic keys available to the one or more wireless transceivers and to the one or more verification units.

In a further implementation form of the first and/or second aspects, one or more of the location certificates further comprise a timestamp indicative of a transmission time of the respective location certificate. One or more of the verification units use the timestamp to timeline the estimated path.

In an optional implementation form of the first and/or second aspects, one or more of the wireless transceivers transmit one or more additional location certificates in case the mobile wireless device exits and re-enters the limited transmission range of the respective wireless transceivers.

In a further implementation form of the first and/or second aspects, one or more of the wireless transceivers are battery-less wireless transceivers powered by energy harvested from the transmission of the mobile wireless device.

In a further implementation form of the third and/or fourth aspects, the limited reception range defines a limited space in the monitored space in proximity to the one or more wireless receivers such that only when located within the limited space the one or more wireless receivers receive the device ID transmitted by the mobile wireless device.

In an optional implementation form of the third and/or fourth aspects, a timeline of the path is estimated according to a timestamp extracted from the one or more location certificates.

In an optional implementation form of the third and/or fourth aspects, one or more of the wireless receivers transmit one or more additional location certificates in case the mobile wireless device exits and re-enters the limited reception range of the respective wireless receivers.

In an optional implementation form of the third and/or fourth aspects, the mobile wireless device is correlated with the associated user based on analysis of one or more images captured at a time of transmission of the location certificate by one or more imaging sensors configured to monitor the predefined location of the one or more wireless receivers.

In an optional implementation form of the third and/or fourth aspects, the path of the associated user through the monitored space is estimated based on detection of the associated user in one or more images captured by one or more imaging sensors deployed in the monitored space.

Other systems, methods, features, and advantages of the present disclosure will be or become apparent to one with skill in the art upon examination of the following drawings and detailed description. It is intended that all such additional systems, methods, features, and advantages be included within this description, be within the scope of the present disclosure, and be protected by the accompanying claims.

Unless otherwise defined, all technical and/or scientific terms used herein have the same meaning as commonly understood by one of ordinary skill in the art to which the invention pertains. Although methods and materials similar or equivalent to those described herein can be used in the practice or testing of embodiments of the invention, exemplary methods and/or materials are described below. In case of conflict, the patent specification, including definitions, will control. In addition, the materials, methods, and examples are illustrative only and are not intended to be necessarily limiting.

Implementation of the method and/or system of embodiments of the invention can involve performing or completing selected tasks automatically. Moreover, according to actual instrumentation and equipment of embodiments of the method and/or system of the invention, several selected tasks could be implemented by hardware, by software or by firmware or by a combination thereof using an operating system.

For example, hardware for performing selected tasks according to embodiments of the invention could be implemented as a chip or a circuit. As software, selected tasks according to embodiments of the invention could be implemented as a plurality of software instructions being executed by a computer using any suitable operating system. In an exemplary embodiment of the invention, one or more tasks according to exemplary embodiments of method and/or system as described herein are performed by a data processor, such as a computing platform for executing a plurality of instructions. Optionally, the data processor includes a volatile memory for storing instructions and/or data and/or a non-volatile storage, for example, a magnetic hard-disk and/or removable media, for storing instructions and/or data. Optionally, a network connection is provided as well. A display and/or a user input device such as a keyboard or mouse are optionally provided as well.

BRIEF DESCRIPTION OF THE SEVERAL VIEWS OF THE DRAWINGS

Some embodiments of the invention are herein described, by way of example only, with reference to the accompanying drawings. With specific reference now to the drawings in detail, it is stressed that the particulars shown are by way of example and for purposes of illustrative discussion of embodiments of the invention. In this regard, the description taken with the drawings makes apparent to those skilled in the art how embodiments of the invention may be practiced.

In the drawings.

DESCRIPTION OF SPECIFIC EMBODIMENTS OF THE INVENTION

Figure 1:
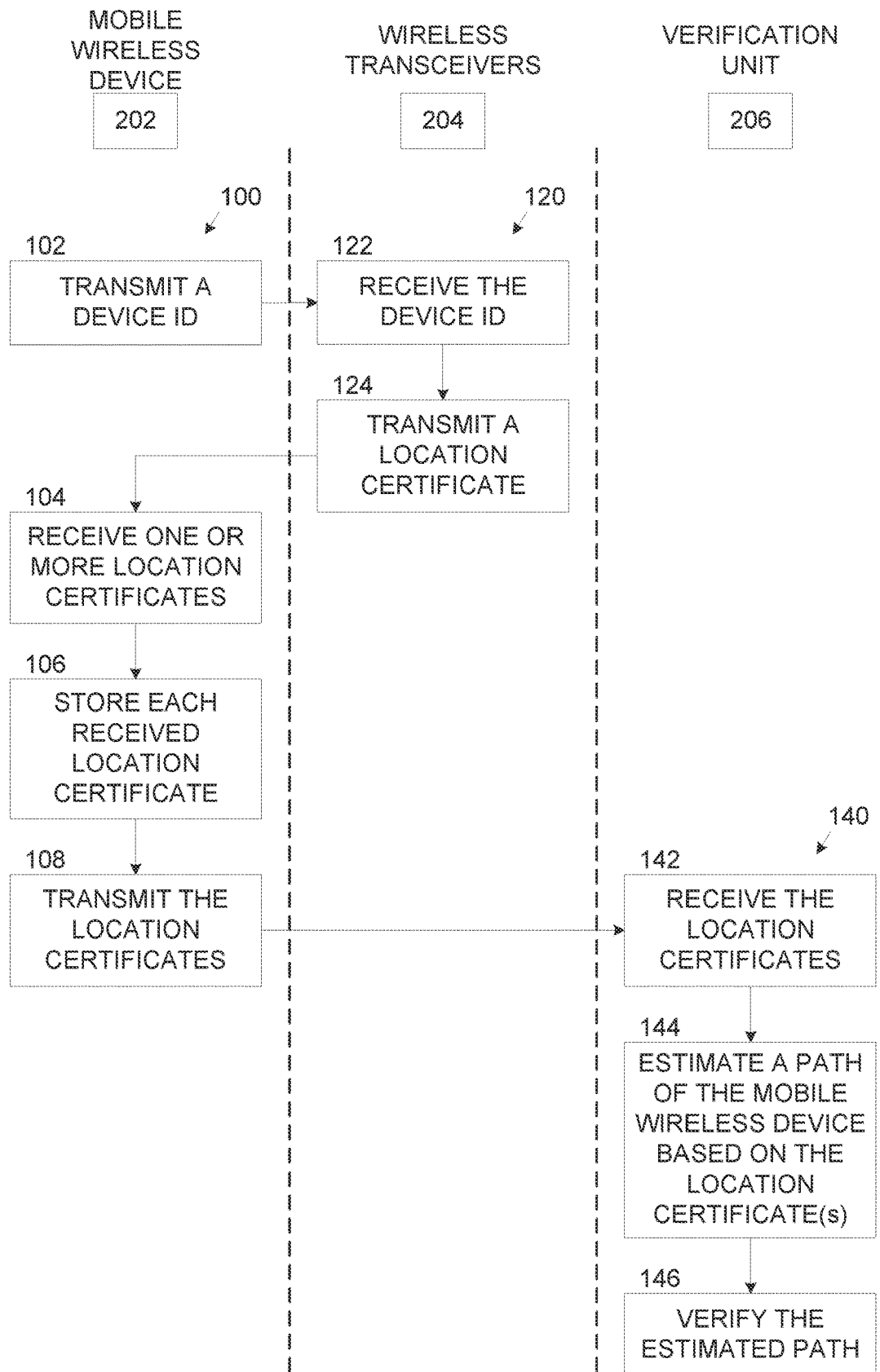
FIG. 1 is a flowchart of an exemplary process of verifying a path of a mobile wireless device in a monitored space based on wireless mapping recorded by the mobile wireless device, according to some embodiments of the present invention.

The present invention, in some embodiments thereof, relates to verifying a path of a mobile wireless device, and, more specifically, but not exclusively, to verifying a path of a mobile wireless device in a monitored space based on wireless mapping of the mobile wireless device by wireless devices deployed in predefined locations in the monitored space.

According to some embodiments of the present invention, there are provided methods, systems, devices and computer program products for verifying a path of mobile wireless devices in monitored spaces based on wireless mapping recorded by each mobile wireless device which thus serves as the carrier of the wireless mapping.

The monitored space which may be a private area and/or a public area, for example, an office area, a building floor, a building, a facility, a school, a hospital, a sports stadium, a train station, an airport and/or the like may be deployed with one or more wireless transceivers located in predefined (fixed) locations in the monitored space. The wireless transceiver(s) may be configured to interact with other wireless devices via one or more wireless communication channels, for example, Radio Frequency (RF), Bluetooth (BT), Bluetooth Low Energy (BLE), ZigBee, Near Field Communication (NFC), Wireless Local Area Network (WLAN, e.g. Wi-Fi) and/or the like. Specifically, the wireless transceivers may be limited range transceivers having a limited transmission range, for example, 0.5 meter, 1 meter, 1.5 meter and/or the like and are thus cable of communicating only with wireless devices located within their limited transmission space (coverage area).

Optionally, one or more of the wireless transceivers may be battery-less wireless transceivers powered by energy harvested from one or more external sources using one or more energy harvesting technologies. For example, the battery-less wireless transceiver(s) may capture energy from RF transmission originating from one or more other wireless devices located in their environment, typically in their immediate environment (close proximity).

One or more mobile wireless devices present and/or moving (traveling) in the monitored space may communicate with one or more of the wireless transceivers deployed in the monitored space over one or more of the wireless communication channels. Specifically, due to the limited range of wireless transceivers, a respective mobile wireless device may communicate with a respective wireless transceiver only when the respective mobile wireless device is within the limited transmission range of the respective wireless transceiver.

Each mobile wireless device may continuously or periodically transmit a device identification (ID) uniquely assigned to the respective mobile wireless device. One or more of the wireless transceivers may intercept the device ID of the respective mobile wireless device and in response may transmit a location certificate to the respective mobile wireless device. Due to the limited range of the wireless transceivers, the respective mobile wireless device may receive the location certificate only when located within the limited transmission range of the respective wireless transceiver(s).

As such, while traveling in the monitored space one or more of the mobile wireless devices may receive and locally store one or more location certificates generated for the respective mobile wireless device(s) by wireless transceivers having their transmission space crossed (entered) by the respective mobile wireless device(s).

To this end, the mobile wireless devices and the wireless transceivers may employ one or more predefined protocols to communicate with each other, specifically to transmit and receive the location certificates.

Each location certificate may include at least the intercepted device ID of the mobile wireless device and a transceiver ID of the respective wireless transceiver which generated and transmitted the respective location certificate. However, one or more of the location certificates may further include a timestamp indicating a transmission time of the respective location certificate. While it is possible that one or more of the wireless transceiver creates the timestamps based on an internal timing reference (e.g. a clock circuit), typically the low end wireless transceivers may obtain the timing reference form the mobile wireless device itself.

Optionally, one or more of the wireless transceivers may encrypt the location certificates they transmit according to one or more cryptographic protocols and/or algorithms using one or more secret cryptographic keys which are not available and thus unknown to the mobile wireless devices.

One or more verification units having wireless connectivity via one or more of the wireless communication channels may be deployed at one or more checkpoint in the monitored space. When arriving at one of the checkpoints, a respective mobile wireless device may transmit to the respective verification unit the location certificate(s) that the respective mobile wireless device collected during its travel in the monitored space. To facilitate this communication, the mobile wireless devices and the verification units may employ one or more predefined protocols.

The verification unit may analyze the location certificate(s) received from the respective mobile wireless device to extract the device ID and the transceiver ID included in each location certificate. Optionally, in case one or more of the location certificates are encrypted, the verification unit having access to the cryptographic key(s) used by the wireless transceiver(s) may first decrypt the location certificate(s) in order to analyze it.

The verification unit may first verify that the device ID extracted from each location certificate matches the device ID of the respective mobile wireless device to ensure that the respective location certificate was indeed originally generated for the respective mobile wireless device.

The verification unit is familiar with the predefined locations of the wireless transceivers in the monitored space, specifically the location of each wireless transceiver in association with its unique transceiver ID. The verification unit may therefore map each wireless transceiver in the monitored space according to its transceiver ID.

Based on the mapping of the wireless transceivers in the monitored space, the verification unit may compute an estimated path for the respective mobile wireless device based on the wireless transceivers that the respective mobile wireless device encountered in the monitored path and are recorded by the location certificates. Moreover, using the timestamp included in one or more of the location certificates, the verification unit may compute an estimated time-lined path for the respective mobile wireless device.

The verification unit may then verify the estimated path of the respective mobile wireless device, for example, by comparing the estimated path to one or more approved pats.

The path verification may be applied to one or more applications which may affect one or more aspects of the verification system and its elements, for example, the type and use of the mobile wireless devices, the deployment locations of the wireless transceivers, the transmission range of the wireless transceivers, the deployment locations of the verification units and/or the like.

In one exemplary application, the path verification may be applied to validate, authenticate and/or otherwise verify one or more users associated with respective mobile wireless devices before allowing the user(s) access one or more restricted areas and/or resources, for example, a restricted room, a restricted terminal and/or the like. In particular, the user(s) may be verified based on verification of their estimated path in the monitored space which is computed based on the wireless mapping extracted from the location certificates provided by the mobile wireless device(s) associated with the user(s) to be verified. In such exemplary applications, the wireless transceivers may be deployed at passage location typically passed by users traveling in the monitored space, for example, entrances, exits, doors, elevators, escalators, split locations (e.g., intersecting corridors, etc.) and/or the like. Moreover, the transmission range of the wireless transceivers may be set to form a wireless transmission space around each wireless transceiver that may be crossed by the users traveling in the monitored space. Furthermore, the verification unit(s) may be deployed at one or more checkpoints or access points to the restricted area(s) and/or resources, for example, at an entrance to a restricted area, next to a restricted terminal, in association with a network access point and/or the like. The verification unit(s) may verify (validate, authenticate) a certain user by comparing its estimated path to one or more approved paths. In case the estimated path complies, optionally with some acceptable deviation, with the approved path(s), the verification unit may determine that the estimated path is a valid and/or legitimate path and the associated user may be granted access to the restricted area and/or resource. However, in case the estimated path significantly deviates from the approved path(s), the verification unit may determine that the estimated path is suspicious which may be indicative that the associated user may be potentially malicious and is thus denied access to the restricted area and/or resource.

In another exemplary application, the path verification may be applied to verify a path of one or more disinfection apparatuses associated with respective mobile wireless devices compared to one or more predefined (approved) paths. The disinfection apparatuses which may be manually and/or automatically operated may apply one or more disinfection and/or sanitization technologies to disinfect one or more surfaces in the monitored space, for example, a door, a table, a floor, a wall, a door knob, a toilet seat, a sink tap and/or the like. In such exemplary applications, the mobile wireless devices may be coupled with the disinfection apparatuses, specifically with an applicator of the disinfection apparatuses, for example, a disinfection light source, a disinfection material spraying nozzle and/or the like. For example, the disinfection apparatus(s) may comprise one or more disinfection light sources configured to project disinfecting light in one or more spectral wave lengths, for example, Ultraviolet (UV), specifically, UVA, UVC and/or the like. The wireless transceivers may be therefore deployed in close spatial association with the surfaces which are the target of the disinfection process, for example, behind, in front, above, below, in close proximity and/or the like. Moreover, the transmission range of the wireless transceivers may be set according to the disinfection technology. For example, a very limited transmission range may be set in case the disinfection apparatus(s) employ a close range applicator which needs to be very close to the target surface for efficient disinfection. However, a longer transmission range may be set in case the disinfection apparatus(s) employ a wide filed applicator which may be significantly distant from the target surface and still ensure efficient disinfection. The verification unit(s) may be deployed at one or more checkpoints and/or maintenance areas where the disinfection apparatus(s) is maintained and where it may typically end the disinfection process. The verification unit(s) may verify the estimated path of the disinfection apparatus by comparing it to one or more approved paths.

Moreover, the verification unit(s) may verify one or more additional parameters of the disinfection process, for example, a projection time of the disinfecting light, for example, the UVA, the UVC and/or the like over each target surface. This may be done to ensure the projection time which is equivalent to an exposure time of the respective target surface to the disinfecting light meets one or more minimum time thresholds known in the art to be sufficient for effectively disinfecting the respective target surface. To this end the verification unit(s) may analyze the estimated path, specifically the estimated time-lined path computed for the disinfection apparatus to determine the duration of time of the light source(s) in front of each target surface which is indicative of the projection time of the disinfecting light on the respective target surface. The verification unit(s) may further compare the projection time to one or more of the time thresholds to verify that the projection time over each target surface was sufficient for effective disinfection.

Verifying the path of mobile wireless devices in a monitored space based on wireless mapping collected and carried by the mobile wireless devices may present major benefits and advantages compared to existing methods for tracking and verifying paths of mobile wireless devices.

First, some of the existing methods and systems may track the paths of the mobile wireless devices based on data collected by one or more geolocation systems and sensors, for example, Global Positioning System (GPS) and/or the like which may be highly inefficient in closed spaces. In contrast, tracking and verifying the mobile wireless devices based on their wireless mapping may be highly suitable for closed spaces having limited size where the wireless transceivers may be easily deployed to generate the wireless mapping for the mobile wireless devices.

Moreover, other existing methods and systems may track the mobile wireless devices based on their connectivity to a local wireless network, for example, a local Wi-Fi network deployed in the monitored space. However, at least some of the mobile wireless devices may not be connected to the local network or they may be connected to one or more other networks, for example, a cellular network thus making it impossible to track them according to their local network connectivity. Using the wireless transceivers on the other hand may allow efficient and constant tracking of all mobile wireless devices present and/or traveling in the monitored space.

Furthermore, due to the limited transmission range of the wireless transceivers, the wireless mapping which maps the mobile wireless devices in the monitored space may provide high resolution accurate mapping since the mobile wireless devices may collect the wireless mapping, i.e., the location certificates only when in close proximity to one or more of the wireless transceivers having a predefined and known location. As such, each location certificate may accurate place the respective mobile wireless device(s) at the specific location of the respective wireless transceiver, optionally at a specific time. This may be highly advantageous compared to existing methods which may track the mobile wireless devices based on their connectivity to the local wireless network, for example, the Wi-Fi which may be deployed using network infrastructure equipment (e.g. access points, routers, etc.) typically having a very long transmission range. Due to the long transmission range, the mobile wireless devices may communicate with the network infrastructure equipment from distant locations making it highly difficult and practically impossible to accurately map the location of the mobile wireless devices in the monitored space.

In addition, since the wireless mapping information, i.e., the location certificate(s) mapping the mobile wireless device in the monitored space is collected, stored, carried and delivered to the verification unit by the mobile device itself, there is no need to deploy communication infrastructure between the wireless transceivers and the verification unit(s) as may be done by the existing methods which may be complex, expensive and prone to faults and failures.

Also, as the wireless transceivers do not need to communicate with any distant device but rather only with the mobile wireless devices when with their limited transmission range, the wireless transceivers may be simple low cost wireless transceivers which may be also highly reliable and easily deployed in the monitored space. Using the battery-less wireless transceivers which are extremely low cost may further reduce the overall costs for deploying the path verification system and may significantly improve coverage of the monitored space by the easily and simply deployable battery-less wireless transceivers.

Lastly, since the location certificates may be encrypted and thus inaccessible to the mobile wireless devices, the mobile wireless devices may be unable to manipulate the wireless mapping in attempt to deceive the verification unit.

According to some embodiments of the present invention, there are provided methods, systems, devices and computer program products for verifying the paths of the mobile wireless devices in the monitored spaces based on the wireless mapping of the mobile wireless devices collected by limited range wireless receivers deployed in the monitored space and configured to transmit the wireless mapping to one or more of the verification units.

As described herein before, one or more of the mobile wireless devices present, moving and/or traveling in the monitored space may continuously and/or periodically transmit their unique device IDs. One or more wireless receivers may intercept the device ID(s) transmitted by the respective mobile wireless device(s). In particular, the wireless receivers may have a very limited reception range such that they may intercept only device ID(s) of mobile wireless devices located with their limited reception range.

As opposed to collecting the wireless mapping, i.e., the location certificates by the mobile wireless devices themselves, the wireless receivers may directly communicate with the verification unit(s) to provide the location certificates.

This approach for verifying the path of the mobile wireless devices based on the wireless mapping may present some benefits and advantages compared to existing methods for verifying a path based on wireless mapping.

First, as described herein before, due to the limited range of the wireless receivers, the wireless mapping extracted from the location certificates may map the mobile wireless devices in the monitored with high resolution and significantly high accuracy.

Moreover, since mobile wireless devices typically broadcast their device ID, for example, when searching for a network access point, when searching to pair a BT device and/or the like, the wireless receivers may intercept the device IDs without directly communicating with the mobile wireless devices. As such there is no need to deploy any special, predefined and/or common communication protocols between the wireless receivers and the mobile wireless devices which may significantly simplify the path verification and may make it available to practically any mobile wireless device detected in the monitored space without the need to installing such communication protocol(s) in the mobile wireless devices.

Before explaining at least one embodiment of the invention in detail, it is to be understood that the invention is not necessarily limited in its application to the details of construction and the arrangement of the components and/or methods set forth in the following description and/or illustrated in the drawings and/or the Examples. The invention is capable of other embodiments or of being practiced or carried out in various ways.

As will be appreciated by one skilled in the art, aspects of the present invention may be embodied as a system, method or computer program product. Accordingly, aspects of the present invention may take the form of an entirely hardware embodiment, an entirely software embodiment (including firmware, resident software, micro-code, etc.) or an embodiment combining software and hardware aspects that may all generally be referred to herein as a "circuit," "module" or "system." Furthermore, aspects of the present invention may take the form of a computer program product embodied in one or more computer readable medium(s) having computer readable program code embodied thereon.

Any combination of one or more computer readable medium(s) may be utilized. The computer readable storage medium can be a tangible device that can retain and store instructions for use by an instruction execution device. The computer readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punch-cards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer program code comprising computer readable program instructions embodied on a computer readable medium may be transmitted using any appropriate medium, including but not limited to wireless, wire line, optical fiber cable, RF, etc., or any suitable combination of the foregoing.

The computer readable program instructions described herein can be downloaded to respective computing/processing devices from a computer readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

The computer readable program instructions for carrying out operations of the present invention may be written in any combination of one or more programming languages, such as, for example, assembler instructions, instruction-set-architecture (ISA) instructions, machine instructions, machine dependent instructions, microcode, firmware instructions, state-setting data, or either source code or object code written in any combination of one or more programming languages, including an object oriented programming language such as Smalltalk, C++ or the like, and conventional procedural programming languages, such as the "C" programming language or similar programming languages.

The computer readable program instructions may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer readable program instructions by utilizing state information of the computer readable program instructions to personalize the electronic circuitry, in order to perform aspects of the present invention.

Aspects of the present invention are described herein with reference to flowchart illustrations and/or block diagrams of methods, apparatus (systems), and computer program products according to embodiments of the invention. It will be understood that each block of the flowchart illustrations and/or block diagrams, and combinations of blocks in the flowchart illustrations and/or block diagrams, can be implemented by computer readable program instructions.

The flowchart and block diagrams in the Figures illustrate the architecture, functionality, and operation of possible implementations of systems, methods, and computer program products according to various embodiments of the present invention. In this regard, each block in the flowchart or block diagrams may represent a module, segment, or portion of instructions, which comprises one or more executable instructions for implementing the specified logical function(s). In some alternative implementations, the functions noted in the block may occur out of the order noted in the figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

Referring now to the drawings, FIG. 1 illustrates a flowchart of an exemplary process of verifying a path of a mobile wireless device in a monitored space based on wireless mapping recorded by the mobile wireless device, according to some embodiments of the present invention.

An exemplary process 100 may be executed by a mobile wireless 202 device traveling in a monitored space to collect wireless mapping information from one or more wireless transceivers 204 deployed in the monitored space which the mobile wireless device passes and communicates with. A complementary exemplary process 120 may be executed by each wireless transceiver 204 interacting with the mobile wireless device.

At one or more checkpoints in the monitored space, the mobile wireless device may provide the wireless mapping information to a respective verification unit 206 which may execute an exemplary process 140 to estimate a path of the mobile wireless device 202 in the monitored space based on the wireless mapping information in order to authenticate, validate and/or authorize a user and/or an apparatus associated with the mobile wireless device 202.

Figure 2:
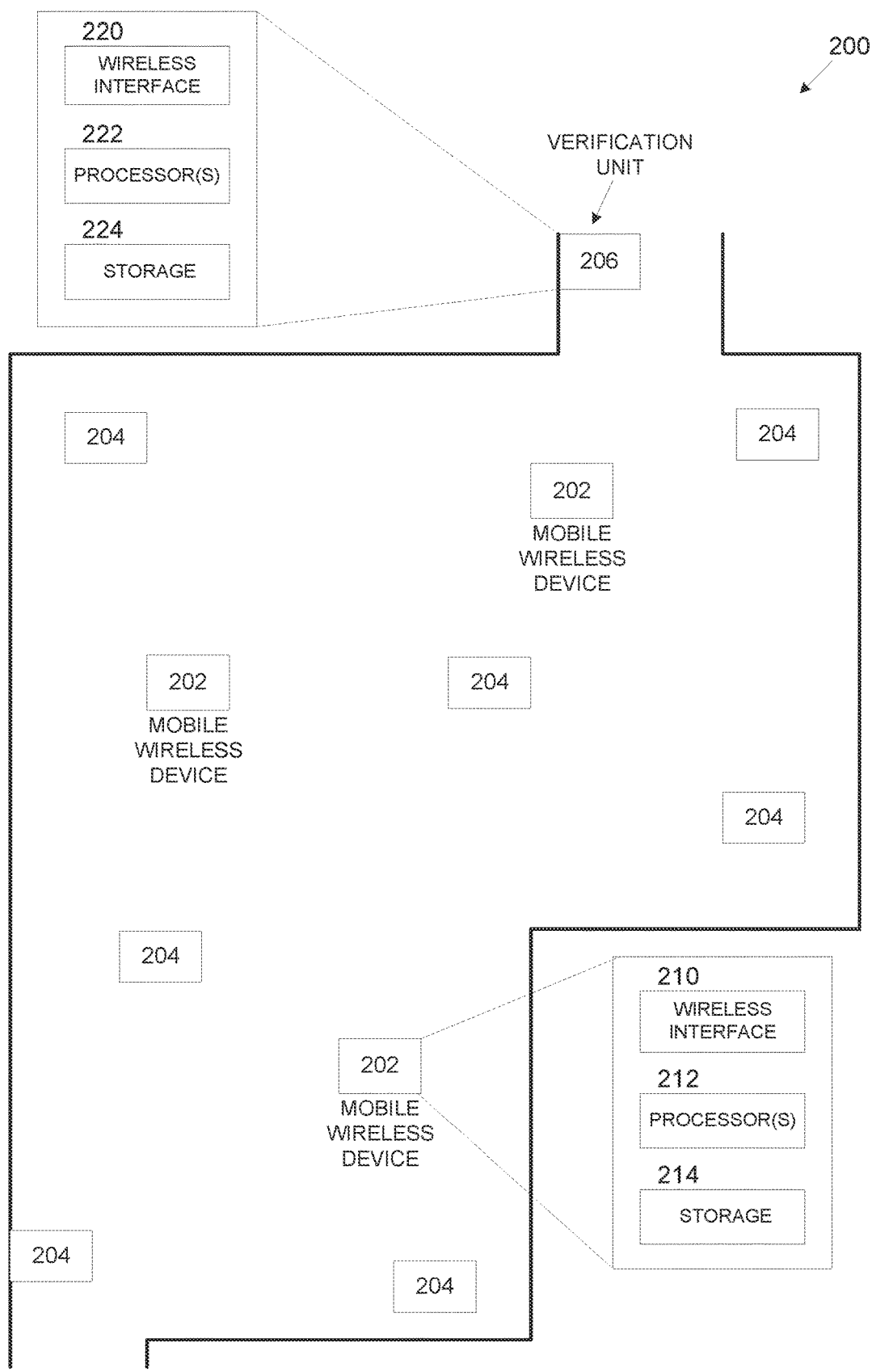
FIG. 2 is a schematic illustration of an exemplary system for verifying a path of a mobile wireless device in a monitored space based on wireless mapping, according to some embodiments of the present invention.

Reference is also made to FIG. 2, which is a schematic illustration of an exemplary system for verifying a path of a mobile wireless device in a monitored space based on wireless mapping, according to some embodiments of the present invention.

An exemplary monitored space 200 which may be a private area and/or a public area, for example, an office area, a building floor, a building, a facility, a school, a hospital, a sports stadium, a train station, an airport and/or the like may be deployed with one or more wireless transceivers 204. The wireless transceivers 204 may operate according to one or more wireless technologies and/or protocols, for example, Radio Frequency (RF), Bluetooth (BT), Bluetooth Low Energy (BLE), ZigBee, Near Field Communication (NFC), Wireless Local Area Network (WLAN, e.g. Wi-Fi) and/or the like.

Each of the wireless transceivers 204 may be deployed at a respective predefined and known static (fixed) location in the monitored space 200, specifically the wireless transceivers 204 may be deployed to provide sufficient coverage of the monitored space 200.

Moreover, the wireless transceivers 204 deployed in the monitored space 200 may be limited range transceivers having a limited transmission range, for example, 0.5 meter, 1 meter, 1.5 meters, 2 meters and/or the like. This means that each of the wireless transceivers 204 may have a very limited transmission space (area), typically a limited radius transmission sphere around the respective wireless transceiver 204 where the radius equals the transmission range. Therefore, only wireless receivers located within the limited transmission range of a respective wireless transceiver 204 may be able to intercept data transmission originating (transmitted by) from the respective wireless transceiver 204.

Optionally, one or more of the wireless transceivers 204 are battery-less wireless transceivers powered by energy harvested from one or more external sources using one or more energy harvesting technologies. Specifically, the wireless transceiver(s) 204 may capture energy from Radio Frequency (RF) transmission originating from one or more other wireless devices. Such battery-less wireless transceivers may be extremely simple and very low cost and may be therefore available in easy deployment forms, for example, a sticker, a label and/or the like which may be highly suitable for wide spread deployment in the monitored space 200.

One or more mobile wireless devices 202 may move and/or be present in a monitored space 200 which may be a private area and/or a public area, for example, an office area, a building floor, a building, a facility, a school, a hospital, a sports stadium, a train station, an airport and/or the like. As such, while moving through the monitored space 200, one or more of the mobile wireless devices 202 may communicate with one or more of the wireless transceivers 204 deployed in the monitored space 200, specifically to collect wireless mapping of the mobile wireless devices 202 in the monitored space 200. In particular, due to the limited transmission range of the wireless transceivers 204, the mobile wireless device 202 may communicate with a respective wireless transceiver 204 only when entering the limited transmission range (area, sphere) of the respective wireless transceiver 204.

According to some embodiments of the present invention, each mobile wireless device 202 may be associated with a respective user traveling in the monitored space and as such may include, for example, a Smartphone, a Smartwatch, a wearable wireless device (e.g. bracelet, tag, card, etc.) and/or the like. Each mobile wireless device 202 associated with a respective associated user may be therefore carried, worn, attached and/or otherwise physically coupled with the respective user such that each mobile wireless device 202 moves together with its respective user in the monitored space 200.

According to other embodiments of the present invention, each mobile wireless device 202 may be associated with a respective disinfection apparatus configured to disinfect one or more surfaces in the monitored space 200, for example, a door, a table, a floor, a wall, a door knob, a toilet seat, a sink tap and/or the like. The disinfection apparatus which may be a manually operated apparatus, and/or an automatic apparatus may apply one or more disinfection and/or sanitization technologies to disinfect the surfaces. For example, the disinfection apparatus may comprise one or more light sources (applicators) which may be operated to project disinfection light on the surface(s) in one or more spectral wave lengths, for example, UV, specifically, UVA, UVC and/or the like. The light source(s) of the disinfection apparatus may be further operated to project the disinfection light according to one or more patterns, for example, a beam width (e.g. wide, narrow, surface distance dependent, etc.), a timing (e.g. continuously, periodically, per instruction, etc.) and/or the like. In another example, the disinfection apparatus may comprise one or more spraying nozzles (applicators) which may be operated to spray one or more disinfection materials on the surface(s). Each mobile wireless device 202 associated with a respective disinfection apparatus may be therefore installed, mounted, attached and/or otherwise physically coupled with the respective disinfection apparatus such that each mobile wireless device 202 moves together with its respective disinfection apparatus in the monitored space 200. Moreover, the mobile wireless device 202 associated with the respective disinfection apparatus may be physically coupled with a disinfection element of the respective disinfection apparatus, for example, the light source(s), the spraying nozzle(s) and/or the like.

Each mobile wireless device 202 may comprise a wireless interface 210, a processor(s) 212 and a storage 214 for storing code (program store) and/or data.

The wireless interface 210 may include one or more wireless interfaces, for example, RF, BT, BLE, ZigBee, NFC, WLAN and/or the like for communicating with one or more other wireless devices.

The processor(s) 212, homogenous or heterogeneous, may include one or more processing nodes arranged for parallel processing, as clusters and/or as one or more multi core processor(s). The processor(s) 212 may execute one or more software modules such as, for example, a process, a script, an application, an agent, a utility, a tool, an Operating System (OS), a driver, a plug-in, a patch, an update and/or the like each comprising a plurality of program instructions stored in a non-transitory medium (program store) such as the storage 214 and executed by one or more processors such as the processor(s) 212. The processor(s) 212 may further integrate, utilize and/or facilitate one or more hardware modules (elements) integrated and/or coupled with the mobile wireless devices 202, for example, a circuit, a component, an Integrated Circuit (IC), an Application Specific Integrated Circuit (ASIC), a Field Programmable Gate Array (FPGA), a Digital Signals Processor (DSP) and/or the like.

The processor(s) 212 may therefore execute one or more functional modules utilized by one or more software modules, one or more of the hardware modules and/or a combination thereof for executing the process 100.

In the embodiments relating to the mobile wireless devices 202 associated with users, the wireless transceivers 204 may be deployed and located in the monitored space 200 to provide sufficient coverage for most and desirably all travel paths possible in the monitored space 200. The wireless transceivers 204 may be therefore deployed to cover possible travel paths of users in the monitored space 200, for example, corridors, halls, room and/or the like, specifically such that the users may cross the limited radius transmission sphere around one or more of the wireless transceivers 204. As such, the wireless transceiver 204 may be deployed at passage locations where users may typical pass while traveling in the monitored space 200, for example, entrances, exits, doors, elevators, escalators, split locations (e.g., intersecting corridors, etc.) and/or the like. While deployed to cover the paths in the monitored space 200, the deployment locations of the wireless transceivers 204 may further depend on the wireless technology and range of the selected wireless transceivers 204.

In the embodiments relating to the mobile wireless devices 202 associated with disinfection apparatuses, the wireless transceivers 204 may be deployed and located in association with the surfaces requiring which are the target of the disinfection procedure executed by one or more of the disinfection apparatuses. As such, the wireless transceivers 204 may be associated with respect to each surface in one or more locations, for example, on, behind, in front, above, below, in close proximity and/or the like. Again, while deployed to provide coverage of the surfaces in the monitored space 200 which are the target of the disinfection procedure, the deployment locations of the wireless transceivers 204 may further depend on the wireless technology and range of the selected wireless transceivers 204 which may optionally depend of the disinfection and/or sanitization technology employed by the disinfection apparatus(s) to disinfect the surface(s). For example, in case the disinfection apparatus employs a close proximity disinfection technology requiring the applicator (e.g. light source and/or the nozzle) to be in very close proximity to the target surface in order to effectively disinfect it, for example, 0.2 meter, 0.5 meter, 1 meter and/or the like, the mobile wireless device 202 may be associated (mounted, integrated, etc.) with the applicator and the wireless transceivers 204 may be configured to have a very limited transmission range which may overlap with the close proximity applicator. However, in case the disinfection apparatus employs a wide filed disinfection technology in which the applicator may be significantly distant from the target surface and still effectively disinfect it, for example, 2 meters, 3 meters and/or the like, the mobile wireless device 202 may be associated with the applicator and the wireless transceivers 204 may be configured to have a relatively large transmission range which may overlap with the wide field applicator.

Furthermore, one or more verification units 206 may be deployed in the monitored space 200 to communicate with the mobile wireless device(s) 202, receive its verify a path of one or more of the mobile wireless devices 202 in the monitored space 200.

The verification units 206 may be deployed at various locations in the monitored space 200 or offsite optionally depending on the verification application. For example, in embodiments relating to the mobile wireless devices 202 associated with users which need to be validated before allowed to access one or more restricted areas and/or resources, for example, a restricted room, a restricted terminal and/or the like, the verification unit(s) 206 may be deployed at one or more of checkpoints or access points to the restricted area(s) and/or resources. In another example, in embodiments relating to the mobile wireless devices 202 associated with users which need to be validated before allowed to access one or more restricted resources, for example, a restricted (secure, protected, etc.) network and/or the like, the verification units 206 may be deployed next and/or in association with one or more network infrastructure equipment, for example, an access point, a router, a switch and/or the like. In another example, in the embodiments relating to the mobile wireless devices 202 associated with disinfection apparatuses, the verification units 206 may be deployed and located at one or more maintenance locations where the disinfection apparatuses are maintained which may be their final stop after completing the disinfection procedure.

Each verification unit 206 may therefore comprise a wireless interface 220 such as the wireless interface 210 for communicating with one or more other wireless devices, a processor(s) 222 such as the processor(s) 212 for executing a verification process to verify the path of the mobile wireless device(s) 220 and a storage 224 such as the storage 214 for storing code (program store) and/or data. The verification unit 206 may execute one or more functional modules to execute the verification process executed which may be utilized by one or more software modules, one or more of the hardware modules and/or a combination thereof.

Optionally, the verification unit(s) 206, may be remote systems which are located on site and/or offsite (e.g. remote server, cloud service, cloud platform, etc.) and are adapted to communicate with the mobile wireless device(s) 202 via one or more on-spot access devices deployed at one or more of the checkpoints, network infrastructure equipment and/or maintenance locations. Moreover, in order to ensure data security, integrity and/or privacy, the communication between the verification unit(s) 206 and the on-spot access device(s) may be secure, for example, encrypted, interception proof and/or the like.

The process 100 may be executed by one or more of the mobile wireless devices 202 moving in any monitored space 200 deployed with one or more of the wireless transceivers 204. As such, the process 100 may be executed by mobile wireless devices 202 associated with users traveling in the monitored space 200 and/or by mobile wireless devices 202 associated with disinfection apparatuses maneuvered, manually and/or automatically to disinfect surfaces in the monitored space 200.

The mobile wireless device 202 may execute the process 100 by executing one or more functional modules, for example, an application stored in the mobile wireless device 202, for example, in the storage 214 and executed by the processor(s) 212. Similarly, each verification unit 206 may execute the process 140 by executing one or more functional modules, for example, an application stored in the verification unit 206, for example, in the storage 224 and executed by the processor(s) 222. Each wireless transceiver 204 may also execute one or more functional modules utilized by one or more software modules executed by a processing circuit of the respective wireless transceiver 204, one or more hardware modules of the respective wireless transceiver 204 and/or a combination thereof.

The mobile wireless device(s) 202, the wireless transceiver(s) 204 and the verification unit(s) 206 may follow one or more common communication and interaction protocols deployed over one or more predefined communication channels to exchange data between them.

As shown at 102, while moving through the monitored space 200, the mobile wireless device 202 may transmit its device identification (ID) via one or more of the wireless channels supported by the wireless interface 210, for example, BT, BLE, ZigBee, WLAN and/or the like. Specifically, the mobile wireless device 202 may transmit its device ID via one or more wireless channels defined by the common communication and interaction protocols employed for communication between the mobile wireless devices 202 and the wireless transceivers 204.

The device ID transmitted by each mobile wireless device 202 may be uniquely associated with the respective mobile wireless device 202 such that each mobile wireless device 202 may be identified according to its associated unique device ID. The device ID may be based on and/or include, for example, a serial number of the mobile wireless device 202, a network Media Access Controller (MAC) address and/or the like.

The mobile wireless device 202 may transmit its device ID according to one or more protocols either standard and/or proprietary which may define one or more transmission parameters for the transmission of the device ID by the mobile wireless device 202. For example, the transmission parameters may define a transmission mode of the device ID, for example, periodic transmission, continuous transmission and/or the like. For the periodic transmission, the transmission parameters may further define a time period between subsequent transmission, for example, 1 second, 2 seconds, 5 seconds and/or the like. In another example, the transmission parameters may define a transmission signal strength, for example, high signal strength, standard signal strength, low signal strength and/or the like in order to define and/or limit the transmission range of the device ID with respect to the location of the mobile wireless device 202.

As shown at 122, one or more wireless transceivers 204 configured to intercept data transmitted over the wireless channel(s), specifically wireless transceiver(s) 204 which are within the transmission range of the mobile wireless device 202, may receive the device ID transmitted from the mobile wireless device 202.

As shown at 124, each wireless transceiver 204 which receives the device ID may transmit in response a location certificate intended for the mobile wireless device 202.

The location certificate may include at least the device ID of the mobile wireless device 202 and a transceiver ID uniquely associated with the respective wireless transceiver 204. The unique transceiver ID assigned to each of the wireless transceivers 204 may be allocated using one or more methods as described for the mobile wireless device 202.

However, the location certificate transmitted by one or more of the wireless transceivers 204 may further include a timestamp indicative of a transmission time of the location certificate from the respective wireless transceiver 204. The wireless transceiver 204 may generate the timestamp based on one or more timing mechanisms. Typically, the wireless transceiver 204 may compute the timestamp based on a timing reference received from the mobile wireless device 202. However, in another example, one or more of the wireless transceivers 204 may compute the timestamp based on one or more internal timing, clock and/or counter circuits. Moreover, one or more of the internal counter circuits may be synchronized according to timing signals, for example, a beacon, a sync and/or the like transmitted periodically by one or more wireless transmitters and intercepted by the wireless transceiver(s) 204.

Optionally, one or more of the wireless transceivers 204 may encrypt the location certificate according to one or more encryption protocol using one or more cryptographic key which are available to the respective wireless transceiver 204 and known to the verification unit(s) 206. It should be noted, that the mobile wireless device 202 may be unable to decrypt encrypted location certificates since it does not have access to the cryptographic key(s) used by the wireless transceiver(s) 204.

As shown at 104, the mobile wireless device 202 may receive the location certificate(s) transmitted by the wireless transceiver(s) 204 in response to the reception of the device ID transmitted by the mobile wireless device 202.

Since the wireless transceivers 204 have a very limited transmission range, the mobile wireless device 202 may receive location certificate(s) only from wireless transceiver(s) 204 which is in close proximity to the mobile wireless device 202 such that the mobile wireless device 202 is located in the limited transmission range of this close proximity wireless transceiver(s) 204.

As such while traveling through the monitored space 200, the mobile wireless device 202 may collect location certificates from one or more of the wireless transceivers 204 deployed in the monitored space 200 which have limited transmission area crossed by the mobile wireless device 202. Moreover, the mobile wireless device 202 may move back and forth, meaning that it may move back to an area in monitored space 200 in which the mobile wireless device 202 was already before. In such case, the mobile wireless device 202 may exit and re-enter the limited transmission range (area) of one or more of the wireless transceivers 204 deployed in the previously visited area and may thus interact again with this wireless transceiver(s) 204. The less transceiver(s) 204 may therefore receive again the device ID of the mobile wireless device 202 and may transmit one or more additional location certificates to the mobile wireless device 202. The location certificates collected by the mobile wireless device 202 may be therefore highly indicative of the path of the mobile wireless device 202 in the monitored space 200.

As shown at 106, the mobile wireless device 202 may store the location certificate(s) received form the wireless transceiver(s) 204 in its local storage, for example, the storage 214.

As shown at 108, at one or more checkpoints, the mobile wireless device 202 may transmit its stored location certificate(s) to a respective verification unit 206 deployed to monitor the respective checkpoint.

As shown at 142, the verification unit 206 deployed at one or more of the checkpoints in the monitored space may receive the location certificate(s) from the mobile wireless device 202 which arrived to the respective checkpoint.

Optionally, in case one or more of the received location certificates are encrypted, the verification unit 206 having access to the cryptographic key(s) used to encrypt the location certificate(s) may use this cryptographic key(s) to decrypt the encrypted location certificate(s).

As shown at 144, the verification unit 206 may estimate the path travelled by the mobile wireless device 202 in the monitored space 200 up to the respective checkpoint.

The verification unit 206 may first analyze each received location certificate to extract the device ID of the mobile wireless device 202 and the transceiver ID of the respective wireless transceiver 204 which generated the respective location certificate. The verification unit 206 may compare between the device ID extracted from each location certificate and the device ID of the mobile wireless device 202 to ensure that the location certificate received from the mobile wireless device 202 was indeed generated for the specific mobile wireless device 202.

The predefined location of the each of the wireless transceivers 204 deployed in the monitored space 200 may be available to the verification unit 206, specifically in association with their transceiver IDs. For example, the verification unit 206 may locally store one or more records, for example, a table, a list, a database and/or the like associating the predefined location each wireless transceiver 204 with its unique transceiver ID. In another example, the verification unit 206 may communicate with one or more remote networked resources, for example, a storage server, a cloud storage service and/or the like which store the predefined location of the wireless transceivers 204 in association with their transceiver IDs to obtain the predefined location the wireless transceiver(s) 204 whose transceiver ID is extracted from the received location certificate(s).

Based on the predefined location of each wireless transceiver 204, the verification unit 206 may estimate the path of the mobile wireless device 202 in the monitored space 200.

Moreover, using the timestamp included in one or more of the location certificates created for the mobile wireless device 202, the verification unit may timeline the estimated path and map it in time to generate a more accurate timelined estimated path expressed both spatially in the monitored space 200 and temporally over time.

A shown at 146, the verification unit 206 may verify the estimated path of the mobile wireless device 202. In particular, the verification unit 206 may verify the estimated path with respect to one or more approved paths comparing between the estimated path and each of the approved path(s). In case of a match between the estimated path and one of the approved path(s), the verification unit 206 may determine that the estimated path is valid and legitimate. However, in case the estimated path does not match any of the approved path(s), the verification unit 206 may determine that the estimated path is suspicious and potentially illegitimate and/or at least partially non-complaint with the approved path(s).

For example, assuming the verification unit 206 is deployed and configured to verify, authenticate and/or validate a user associated with the mobile wireless device 202 in order to grant/deny the associated user access to a restricted area and/or a restricted resource. Specifically, the verification unit 206 may verify the associated user by comparing the estimated path with one or more paths approved for users in the monitored space 200. In case the estimated path of the associated user matches one of the approved path(s), the verification unit 206 may determine that the associated user is a legitimate user and may grant him access to the restricted area and/or resource. However, in case the estimated path of the associated user does not match any of the approved path(s), the verification unit 206 may determine that the associated user is potentially not a legitimate user and may deny him access to the restricted area and/or resource.

In another example, assuming the verification unit 206 is deployed and configured to verify the path of a disinfection apparatus associated with the mobile wireless device 202 in order to verify that the associated disinfection apparatus is operated to disinfect one or more of the surfaces in the monitored space 200 according to a predefined (approved) path. In case the estimated path of the associated disinfection apparatus matches the predefined approved path, the verification unit 206 may determine that the associated disinfection apparatus successfully disinfected the surfaces defined by the predefined approved path. However, in case the estimated path of the associated disinfection apparatus does not match the predefined path, the verification unit 206 may determine that the associated disinfection apparatus failed to effectively disinfect at least some of the surfaces defined by the predefined approved path and/or part thereof.

As part of the path verification, the verification unit 206 may further verify one or more additional parameters of the disinfection process conducted by the disinfection apparatus. For example, the verification unit 206 may verify a projection time of the disinfecting light, for example, the UVA, the UVC and/or the like over each target surface in order to ensure that the projection time complies with one or more minimum time thresholds. The projection time which is naturally equivalent to an exposure time of the respective target surface to the disinfecting light must be sufficient as known in the art for effectively disinfecting the respective target surface. The verification unit 206 may therefore analyze the estimated path, specifically the estimated time-lined path computed for the disinfection apparatus to determine the duration of time of the light source(s) in front of each target surface which is indicative of the projection time of the disinfecting light on the respective target surface. The verification unit 206 may than compare the projection time to one or more of the time thresholds to verify that the exposure time of each target surface to the disinfecting light is sufficient for effective disinfection.

The verification unit 206 may apply several techniques for analyzing the estimated time-lined path computed for the disinfection apparatus. For example, one or more of the wireless transceivers 204 associated with one or more of the target surfaces may generate and transmit to the disinfection apparatus multiple location certificates during the time that the disinfection apparatus is located within the transmission range of the respective wireless transceiver 204. The wireless transceiver(s) 204 may periodically transmit such repetitive location certificates, for example, every 0.5 second, every second, and/or the like. Assuming that the location certificates include timestamps, the estimated time-lined path computed for the disinfection apparatus based on the location certificates may therefore reflect the duration of time that the disinfection apparatus was within the transmission range of the respective wireless transceiver 204 which is indicative of the projection time of the disinfecting light over the respective target surface associated with the respective wireless transceiver 204. The verification unit 206 may therefore compare the exposure time over one or more of the target surfaces as derived from the estimated time-lined path to one or more of the time thresholds to verify that the exposure time of each target surface to the disinfecting light is sufficient for effective disinfection. In another example, assuming multiple wireless transceivers 204 are deployed along a certain target surface, specifically such that the transmission ranges of these wireless transceivers 204 do not overlap. While the disinfection apparatus moves to disinfect the certain target surface it may communicate with the wireless transceivers 204 deployed along the certain target surface to collect respective location certificates which may include timestamps. The estimated time-lined path computed for the disinfection apparatus based on the location certificates may therefore reflect the time at which the disinfection apparatus reached each of the wireless transceivers 204. Analyzing the estimated time-lined path, the verification unit 206 may compute the speed of the disinfection apparatus while moving with respect to the certain target surface. The verification nit 206 may further drive from the speed a projection time of the disinfecting light over each segment of the certain target surface. The verification unit 206 may then compare the projection time over each segment to one or more of the time thresholds to verify that the exposure time of each segment of the certain target surface to the disinfecting light is sufficient for effective disinfection.

The verification unit 206 may further analyze the estimated path with respect to a layout of the monitored space 200, for example, a geometry, a map of entry/exit points, corridors, rooms, halls, elevators, escalators and/or the like.

Moreover, based on the analysis of the estimated path, specifically the time-lined estimated path with respect to the layout of the monitored space, the verification unit 206 may further estimate a movement speed of the mobile wireless device 202 in the monitored space 200 which may be further used to verify the estimated path.

Figure 3:
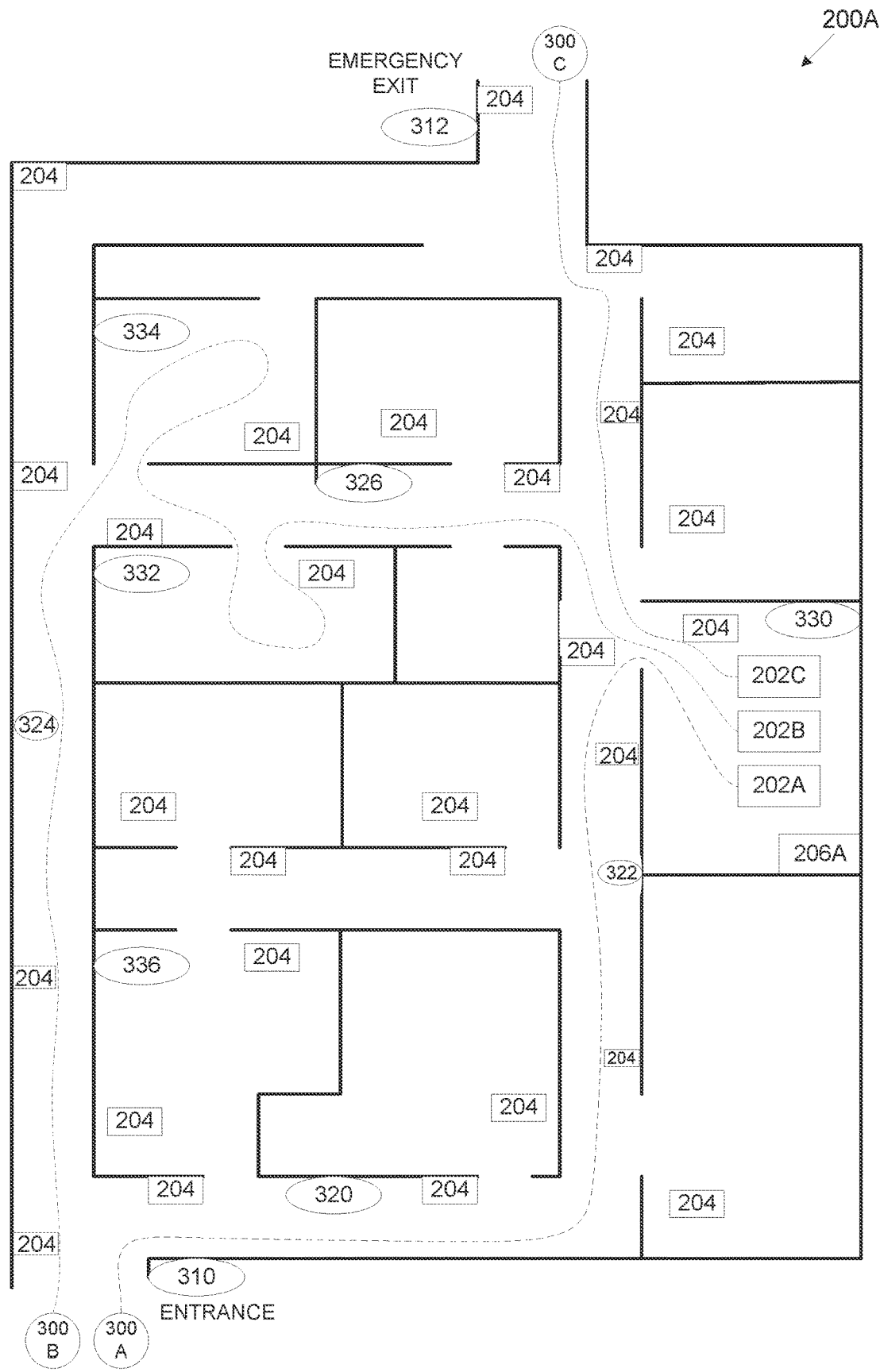
FIG. 3 is a schematic illustration of exemplary travel paths of mobile wireless devices evaluated for path verification in a first exemplary monitored space, according to some embodiments of the present invention.

Reference is now made to FIG. 3, which is a schematic illustration of exemplary travel paths of mobile wireless devices evaluated for path verification in a first exemplary monitored space, according to some embodiments of the present invention.

An exemplary monitored space 200A, for example, an offices site such as the monitored space 200 may comprise a plurality of rooms, for example, an office, a cafeteria, toilets, a conference room, a hall, a library, a copy room and/or the like accessible form one or more of a plurality of corridors. The monitored offices site 200A may be entered from a single entrance 310 and from an emergency exit 312 which is typically closed.

A plurality of wireless transceivers such as the wireless transceiver 204 may be deployed at various locations in the monitored offices site 200A, specifically at passage locations where users may typical pass while traveling in the monitored offices site 200A, for example, at the entrance 310, at the emergency exit 312, in one or more of the corridors, in one or more of the rooms and/or the like. Moreover, the wireless transceivers 204 may be deployed at locations which are typically passed by traveling users, for example, room doors, corridor corners and/or the like. As such, the wireless transceivers 204 may be deployed to effectively cover the monitored offices site 200A, in particular the travel paths in the monitored offices site 200A.

A verification unit 206A such as verification unit 206 may be deployed in the office 330 to validate, authenticate and/or otherwise verify users attempting to access (connect to) a certain restricted resource, for example, a network of the monitored offices site 200A via an access point located in the office 330. In order to verify that one or more users attempting to connect to the access point in office 330 are allowed to do so, the verification unit 206A may verify the path travelled by the user to the office 330.

A first user associated with a first mobile wireless device 202A may travel to a certain room 330, for example, an office in a first path 300A, a second user associated with a second mobile wireless device 202B may travel to the office 330 in a second path 300B and a third user associated with a third mobile wireless device 202C may travel to the office 330 in a third path 300C.

As seen, the path 300A starts from the entrance 310 and goes through corridors 320 and 322 to the office 330. The mobile wireless device 202A may therefore communicate with one or more of the wireless transceivers 204 located along the path 300A to collect respective location certificates, for example, the wireless transceiver 204 deployed at the entrance 310, one or more of the wireless transceivers 204 deployed in the corridors 320 and/or 322 and/or the wireless transceiver 204 deployed in the office 330. The path 300B also starts from the entrance 310 and goes through corridor 324 to room 334, out of the room 334 to room 332, out of the room 332 and through corridor 326 to the office 330. The mobile wireless device 202B may therefore communicate with one or more of the wireless transceivers 204 located along the path 300B to collect respective location certificates, for example, the wireless transceiver 204 deployed at the entrance 310, one or more of the wireless transceivers 204 deployed in the corridor 324, one or more of the wireless transceivers 204 deployed in the rooms 332 and/or 334, one or more of the wireless transceivers 204 deployed in the corridor 326 and/or the wireless transceiver 204 deployed in the office 330. The path 300C starts from the emergency exit 312 and goes through corridor 322 to the office 330. The mobile wireless device 202C may therefore communicate with one or more of the wireless transceivers 204 located along the path 300C to collect respective location certificates, for example, the wireless transceiver 204 deployed at emergency exit 312, one or more of the wireless transceivers 204 deployed in the corridor 322 and/or the wireless transceiver 204 deployed in the office 330.

Assuming that after arriving to the office 330, each of the three users may attempt to access the access point located in the office 330 in order to connect to the network of the monitored offices site 200A. The verification unit 206A may therefore validate and/or authenticate the respective users based on verification of the verify the paths 300A, 300B and 300C respectively and accordingly grant or deny the respective user access to the network.

For example, the verification unit 206A may receive the location certificates collected by the mobile wireless device 202A along the path 300A and may extract the transceiver IDs of the respective wireless transceivers 204 that the mobile wireless device 202A passed and interacted with along the path 300A. The verification unit 206A may then compute an estimated path 300A according to the predefined locations of the respective wireless transceivers 204. As described herein before, the verification unit 206A may further use the timestamp included in one or more of the location certificates to compute a time-lined estimated path 300A. The verification unit 206A may compare the estimated path 300A to one or more approved paths leading to the office 300, in particular an approved path which is a straight route from the entrance 310 to the office 330 and may determine that the estimated path 300A is a valid path. Based on this determination the verification unit 206A may verify the user associated with the mobile wireless device 202A and may grant him access to the access point located in the office 330 to connect to the network.

In another example, the verification unit 206A may receive the location certificates collected by the mobile wireless device 202B along the path 300B and may extract the transceiver IDs of the respective wireless transceivers 204 that the mobile wireless device 202B passed and interacted with along the path 300B. The verification unit 206A may then compute an estimated path 300B optionally a time-lined estimated path 300B according to the predefined locations of the respective wireless transceivers 204. The verification unit 206A may than compare the estimated path 300B to one or more of the approved paths leading to the office 330 and may determine that the estimated path 300B is highly suspicious as it does not follow a direct route to the office 330 but rather goes through the rooms 334 and 332 before finally arriving to the office 330. The suspicious estimated path 300B may be indicative of an unauthorized user sneaking though the monitored offices site 200A in attempt to locate an access point for connecting to the network for one or more potentially malicious goals. Based on this determination the verification unit 206A may deny the user associated with the mobile wireless device 202B access to the access point located in the office 330 to prevent him from connecting to the network.

In another example, the verification unit 206A may receive the location certificates collected by the mobile wireless device 202C along the path 300C and may extract the transceiver IDs of the respective wireless transceivers 204 that the mobile wireless device 202C passed and interacted with along the path 300C. The verification unit 206A may then compute the estimated path 300C optionally a time-lined estimated path 300C according to the predefined locations of the respective wireless transceivers 204. The verification unit 206A may than compare the estimated path 300C to one or more of the approved paths leading to the office 330 and may determine that the estimated path 300C is highly suspicious since it starts from the emergency exit 312 which is not typically used for entering the monitored office site 200A. The suspicious estimated path 300C may be also indicative of an unauthorized user sneaking though the emergency exit 312 into the monitored offices site 200A in attempt to locate an access point for connecting to the network for one or more potentially malicious goals. Based on this determination the verification unit 206A may deny the user associated with the mobile wireless device 202B access to the access point located in the office 330 to prevent him from connecting to the network.

Optionally, the verification unit 206 analyzes the estimated path with respect to one or more of the approved path(s) according to one or more deviation patterns.

For example, assuming the path verification is applied to verify users associated with mobile wireless devices 202 based on their path in the monitored space 200, for example, the monitored office site 200A. One or more deviation patterns may be defined to indicate that a user heading for the office 330 may deviate from the straight approved path leading to the office 330, for example, to room 336 which may be, for example, the toilets or a cafeteria or some other public space. The deviation pattern(s) may further define a minimum and/or maximum time periods that a deviating user is allowed to stay in the room 336. Therefore, in case verification unit 206A determines that the estimated path of one or more of the users, for example, the estimated path 300A computed for the user associated with the mobile wireless device 202A goes through the room 336 and optionally does not exceed the minimum and/or maximum allowed time periods, the verification unit 206A may still positively verify this user and may grant him access to the access point located in the office 330 for connecting to the network.

In another example, assuming the path verification is applied to verify the path of a disinfection apparatus. One or more deviation patterns may be defined to indicate that a disinfection apparatus operated to disinfect three different surfaces in the monitored space 200 may do so in one or more orders which may affect their path through the monitored space 200. For example, the deviation pattern(s) may define a first approved path of a certain disinfection apparatus may start from a first surface going to a second surface and finishing with a third surface before going to a maintenance point serving as a checkpoint where a certain verification unit 206 may verify the path of the certain disinfection apparatus. However, the deviation pattern(s) may also define a second approved path for the certain disinfection apparatus which may start from the third surface going to the first surface and finishing with the second surface before going to the maintenance point where the verification unit 206 may verify the path of the certain disinfection apparatus.

According to some embodiments of the present invention, the path verification process may be conducted base on location certificates collected by one or more verification units 206 directly from one or more wireless devices, specifically, one or more wireless receivers deployed in the monitored space 200.

Figure 4:
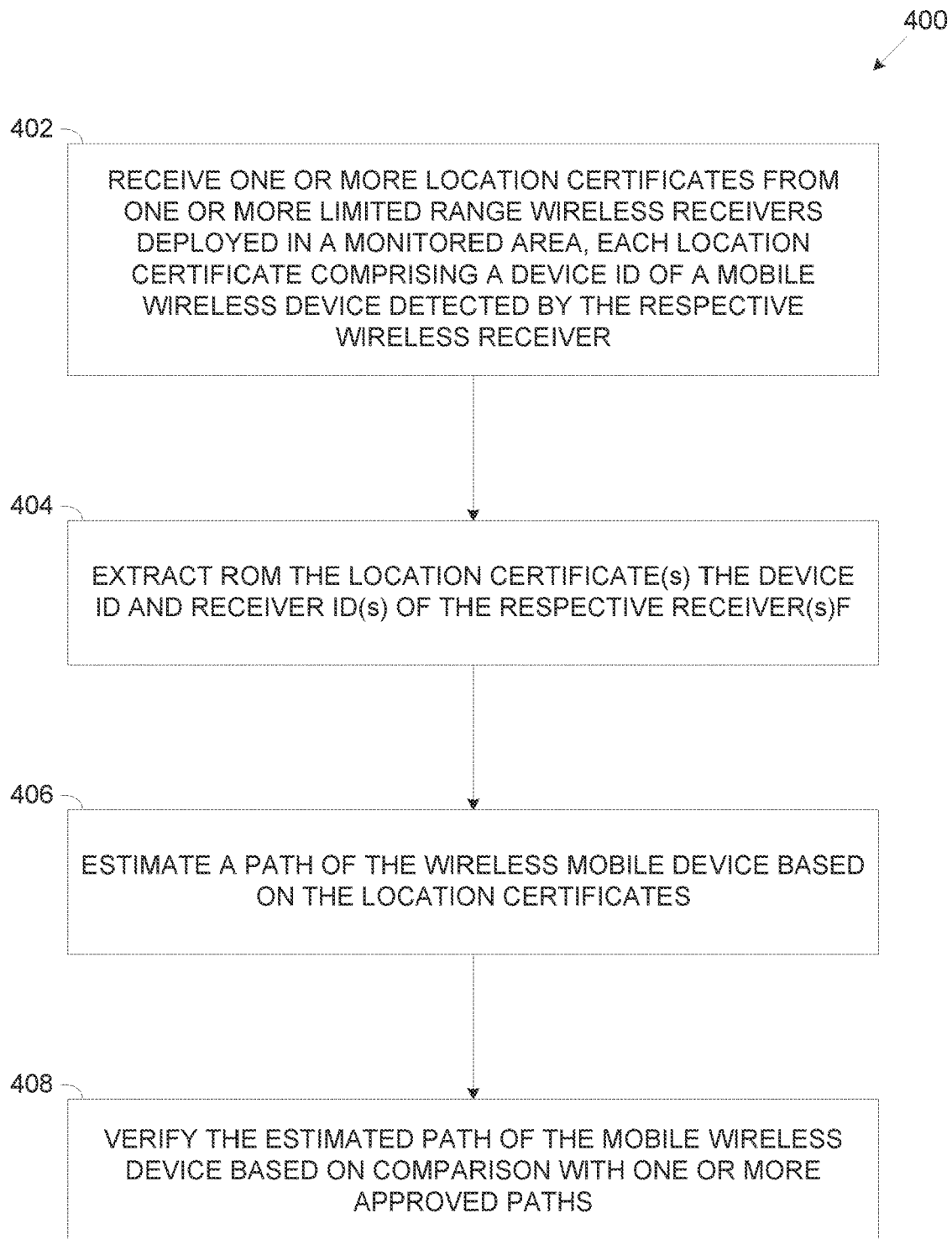
FIG. 4 is a flowchart of an exemplary process of verifying a path of a mobile wireless device in a monitored space based on wireless mapping recorded by wireless receivers deployed I the monitored space, according to some embodiments of the present invention.

Reference is now made to FIG. 4, which is a flowchart of an exemplary process of verifying a path of a mobile wireless device in a monitored space based on wireless mapping recorded by wireless receivers deployed I the monitored space, according to some embodiments of the present invention. An exemplary process 400 may be executed by each of one or more verification units such as the verification unit 206 deployed in a monitored space such as the monitored space 200.

As described in detail herein before, each verification unit 206 may be deployed at a respective checkpoint in the monitored space 200 to verify the path of one or more mobile wireless devices such as the mobile wireless device 202 each associated with a respective user or a respective disinfection apparatus as described in detail herein before.

One or more wireless receivers may be deployed in the monitored space to intercept data transmitted over one or more wireless channels according to one or more wireless technologies and/or protocols, for example, RF, BT, BLE, ZigBee, NFC, WLAN and/or the like. Each of the wireless receivers may be deployed at a respective predefined and known static (fixed) location in the monitored space 200, specifically the wireless receivers may be deployed to provide sufficient coverage of the monitored space 200.

Moreover, the wireless receivers deployed in the monitored space 200 may be limited range receivers having a limited reception range, for example, 0.5 meter, 1 meter, 1.5 meters, 2 meters and/or the like. The limited reception range may define, for each wireless receiver, a respective limited reception space in the monitored space 200 in proximity to the respective wireless receiver. This means that each of the wireless receivers may have a respective very limited reception area, typically a limited radius reception sphere around the respective wireless receiver where the radius equals the reception range. Therefore, each wireless receiver may intercept data transmitted by (originating from) one or more wireless transmitters located within the limited reception range of the respective wireless receiver.

Each of the wireless receivers may be connected to one or more of the verification units 206 via one or more wired and/or wireless channels deployed in the monitored space 200, for example, a serial channel, a Controller Area Network (CAN) bus, a Local Area Network (LAN), an RF link and/or the like.

While the mobile wireless device(s) 202 may not execute a specific and/or dedicated application to support the path verification, one or more of the mobile wireless devices 202 may typically continuously or periodically transmit a unique ID which may serve as a device ID for uniquely identifying the respective mobile wireless device 202. For example, one or more of the mobile wireless devices 202 may attempt to connect to a WLAN network and may thus broadcast its MAC address. In another example, one or more of the mobile wireless devices 202 may search to connect to a BT device or controller and may thus broadcast its BT ID. Therefore, while located, present and/or traveling in the monitored space 200, one or more of the mobile wireless device(s) 202 may transmit its unique device ID either continuously or periodically. One or more of the wireless receivers may therefore intercept the device ID transmitted by one or more of the mobile wireless device(s) 202 in the monitored space 200. However, due to the limited reception range of each of the wireless receivers, a respective wireless receiver may intercept only device ID(s) of mobile wireless device(s) 202 which are within the limited reception area of the respective wireless receiver.

As shown at 402, the process 400 starts with the verification unit 206 receiving one or more location certificates from one or more of the wireless receivers 504 deployed in the monitored space 200 which may communicate with verification unit via one or more of the before. The wireless receivers may connect to the verification unit(s) 206 via one or more wired and/or wireless channels deployed in the monitored space 200.

As described herein before, each of the location certificates received from each of the wireless receivers may include at least the device ID of one of the mobile wireless devices 202 which entered the limited reception range of the respective wireless receiver and the receiver ID of the respective wireless receiver.

Optionally, one or more of the location certificates further includes a timestamp computed by the respective wireless receiver(s) 504 to indicate the reception time of the device ID of the respective mobile wireless devices 202 which entered the limited reception range of the respective wireless receiver. Typically, the wireless receivers 504 may compute the timestamp based on a timing reference received from the mobile wireless device 202. However, in another example, one or more of the wireless receivers 504 may compute the timestamp based on one or more internal timing, clock and/or counter circuits. Moreover, one or more of the internal counter circuits may be synchronized according to timing signals, for example, a beacon, a sync and/or the like transmitted periodically by one or more wireless transmitters and intercepted by the wireless receiver(s) 504.

Optionally, one or more of the location certificates is encrypted according to one or more of the cryptographic protocols and/or algorithms using one or more cryptographic keys available to one or more of the wireless receivers and to the verification unit 206.

As described for the process 100 and the monitored space 200, one or more of the wireless receivers may generate a plurality of location certificates for each of one or more of the mobile wireless devices 202 in case the respective mobile wireless device 202 goes in and out of the limited reception space of the respective wireless receiver.

As shown at 404, the verification unit 206 may analyze each received location certificate received from each wireless receiver to extract the device ID of the mobile wireless device 202 documented by the respective location certificate and the receiver ID of the respective wireless receiver.

The verification unit 206 may further arrange the received location certificates, specifically the wireless mapping information, i.e. the receiver IDs according to the device IDs of the mobile wireless device(s) 202. In other words, the verification unit may correlate each of the received location certificates with a respective mobile wireless device 202 such that each mobile wireless device 202 is associated with all location certificates documenting the respective mobile wireless device 202.

As shown at 406, the verification unit 206 may estimate the path of one or more of the mobile wireless device(s) 202 in the monitored space 200, specifically, the path of mobile wireless device(s) 202 which arrive at the checkpoint in which the verification unit 206 is deployed.

The verification unit 206 may estimate the path of the mobile wireless device 202 based on the predefined locations of the wireless receivers deployed in the monitored space 200 which are available to the verification unit 206 in a same manner as described herein before for the predefined locations of the wireless transceivers 204. In particular, the verification unit 206 may extract the receiver ID from each location certificate associated with the respective mobile wireless device 202 and since the verification unit 206 may associate between the extracted receiver IDs and the predefined locations of the wireless receivers, the verification unit 206 may identify the predefined locations of the wireless receivers which created the location certificates for the respective mobile wireless device 202. Based on the predefined locations of the wireless receive, the verification unit 206 may therefore compute the estimated path of the respective mobile wireless device 202 in the monitored space 200.

As shown at 408, the verification unit 206 may verify the estimated path of the mobile wireless device 202 by comparing between the estimated path and one or more approved paths as described in step 146 of the process 100. In case of a match between the estimated path and one of the approved path(s), the verification unit 206 may determine that the estimated path is valid and legitimate. However, in case the estimated path does not match any of the approved path(s), the verification unit 206 may determine that the estimated path is suspicious and potentially illegitimate and/or at least partially non-complaint with the approved path(s).

Again, as described in step 146, based on the determination of the path verification, the verification unit 206 may grant or deny access to the restricted area and/or the restricted resource to the user associated with the respective mobile wireless device 202 in case the path verification is directed to verify users associated with mobile wireless devices 202. Additionally and/or alternatively, based on the determination of the path verification, the verification unit 206 may determine whether the disinfection apparatus associated with the respective mobile wireless device 202 followed its predefined (planned) path in case the path verification is directed to verify the paths of disinfection apparatuses.

Figure 5:
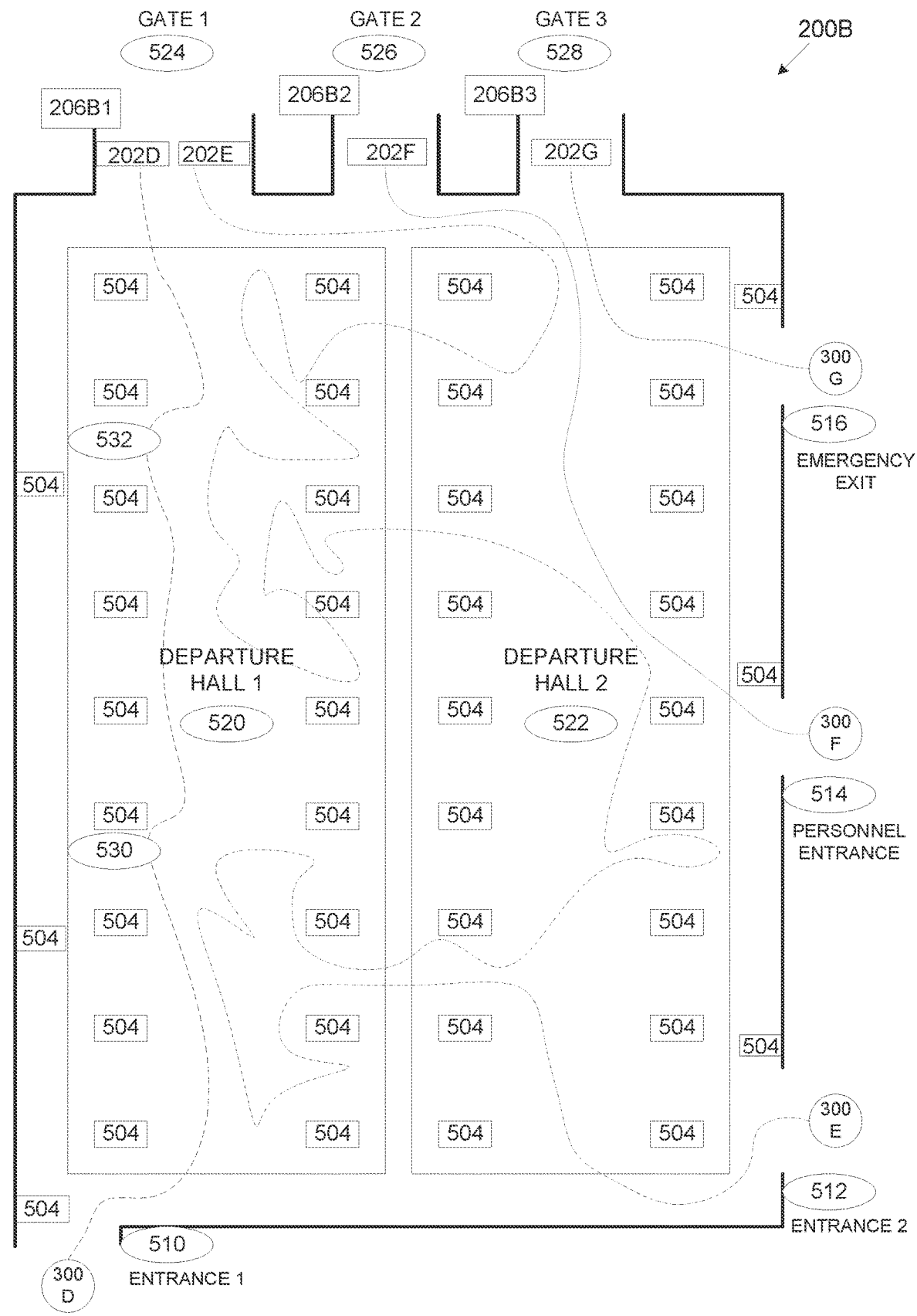
FIG. 5 is a schematic illustration of exemplary travel paths of mobile wireless devices evaluated for path verification in a second exemplary monitored space, according to some embodiments of the present invention.

Reference is also made to FIG. 5, which is a schematic illustration of exemplary travel paths of mobile wireless devices evaluated for path verification in a second exemplary monitored space, according to some embodiments of the present invention.

An exemplary monitored space 200B, for example, an airport such as the monitored space 200 may comprise a plurality of departure halls, for example, a first departure hall 520 and a second departure hall 522 leading to a plurality of gates, for example, a first gate 524, a second gate 526 and a third gate 528. The two departure halls 520 and 522 may be entered from a plurality of entrances, for example, a first public entrance 510, a second public entrance 512, a personnel-only entrance 514 and an emergency exit 516.

A plurality of wireless receivers 504 may be deployed at various locations in the airport 200B, specifically at passage locations where passengers (users) may typical pass while traveling in the airport 200B, for example, users flying out of the airport 200B who travel towards the gates in order to board an airplane. The wireless receivers 504 may be therefore deployed to effectively cover the airport 200B to traveling passengers, for example, at the entrances 510 and 512, at the personnel-only entrance 514, at the emergency exit 518, in each of the departure halls 520 and 522, at the gates 524, 526, 528 and/or the like.

One or more verification units 206B such as the verification unit 206 may be deployed in the airport 200B, for example, a first verification unit 206B1 may be deployed at the first gate 514, a second verification unit 206B2 may be deployed at the second gate 516 and a third verification unit 206B3 may be deployed at the third gate 518.

A first passenger associated with a first mobile wireless device 202D may travel to the first gate 524 in a first path 300D, a second passenger associated with a second mobile wireless device 202E may also travel to the first gate 524 in a second path 300E, a third passenger associated with a third mobile wireless device 202F may travel to the second gate 526 in a third path 300F and a fourth passenger associated with a fourth mobile wireless device 202G may travel to the third gate 528 in a first path 300D.

As seen, the path 300D starts from the first entrance 510 and goes through the first departure hall 520 to the first gate 524. Since the mobile wireless device 202D may continuously or periodically transmit its device ID, one or more of the wireless receivers 504 located along the path 300D may intercept the device ID of the mobile wireless device 202D and may transmit respective location certificates to one or more of the verification units 206B1, 206B2 and/or 206B3. For example, the wireless receiver 504 deployed at the first entrance 510 s well as one or more of the wireless receivers 504 deployed in the first departure hall 520 may intercept the device ID of the mobile wireless device 202D.

The path 300E starts from the second entrance 512 and goes through both departure halls 520 and 522 to the first gate 524. Since the mobile wireless device 202E may continuously or periodically transmit its device ID, one or more of the wireless receivers 504 located along the path 300E may intercept the device ID of the mobile wireless device 202E and may transmit respective location certificates to one or more of the verification units 206B1, 206B2 and/or 206B3. For example, the wireless receiver 504 deployed at the second entrance 512, one or more of the wireless receivers 504 deployed in the first departure hall 520 and/or one or more of the wireless receivers 504 deployed in the second departure hall 522 may intercept the device ID of the mobile wireless device 202E.

The path 300F starts from the personnel-only entrance 514 and goes through the second departure hall 522 to the second gate 526. Since the mobile wireless device 202F may continuously or periodically transmit its device ID, one or more of the wireless receivers 504 located along the path 300F may intercept the device ID of the mobile wireless device 202F and may transmit respective location certificates to one or more of the verification units 206B1, 206B2 and/or 206B3. For example, the wireless receiver 504 deployed at the personnel-only entrance 514 as well as one or more of the wireless receivers 504 deployed in the second departure hall 522 may intercept the device ID of the mobile wireless device 202F.

The path 300G starts from the emergency exit 516 personnel-only entrance 514 and goes through the second departure hall 522 to the third gate 528. Since the mobile wireless device 202G may continuously or periodically transmit its device ID, one or more of the wireless receivers 504 located along the path 300G may intercept the device ID of the mobile wireless device 202G and may transmit respective location certificates to one or more of the verification units 206B1, 206B2 and/or 206B3. For example, the wireless receiver 504 deployed at the emergency exit 516 as well as one or more of the wireless receivers 504 deployed in the second departure hall 522 may intercept the device ID of the mobile wireless device 202F.

When the passengers arrive at one of the gates 524, 526 and/or 528, the passengers may be authenticated, validated and/or otherwise verified by a respective verification unit 206B deployed at the respective gate according to their path in the airport 200B.

For example, when the passenger associated with the mobile wireless device 202D arrives at the first gate 524, the verification unit 206B1 may analyze all the location certificates associated with the mobile wireless device 202D which were received from the one or more of the wireless receivers 504, specifically the wireless receivers 504 located along the path 300D. The verification unit 206B1 may extract the receiver IDs of the respective wireless receivers 504 that intercepted the device ID of the mobile wireless device 202D and transmitted respective location certificates. The verification unit 206B1 may then compute an estimated path 300D according to the predefined locations of the respective wireless receivers 504. As described herein before, the verification unit 206B1 may further use the timestamp included in one or more of the location certificates to compute a time-lined estimated path 300D. The verification unit 206B1 may compare the estimated path 300A to one or more approved paths leading to the first gate 524, in particular an approved path which is a straight route from the first entrance 510 to the first gate 524 and may determine that the estimated path 300D is a valid and legitimate path. Based on this determination, the verification unit 206B1 may verify the user associated with the mobile wireless device 202D and may classify him as a verified legitimate passenger.

In another example, when the passenger associated with the mobile wireless device 202E arrives at the first gate 524, the verification unit 206B1 may analyze all the location certificates associated with the mobile wireless device 202E which were received from the one or more of the wireless receivers 504, specifically the wireless receivers 504 located along the path 300E. The verification unit 206B1 may extract the receiver IDs of the respective wireless receivers 504 that intercepted the device ID of the mobile wireless device 202E and transmitted respective location certificates. The verification unit 206B1 may then compute an estimated path 300E according to the predefined locations of the respective wireless receivers 504. The verification unit 206B1 may further use the timestamp included in one or more of the location certificates to compute a time-lined estimated path 300E. The verification unit 206B1 may compare the estimated path 300E to one or more approved paths leading to the first gate 524 and may determine that the estimated path 300E is highly suspicious as it includes a lot of incoherent movement patterns. The incoherent movement patterns starting from entering the airport 200B at the second gate 512 which is the furthest from the first gate 524 and followed by a plurality of rapid transitions between the first and second departure halls 520 and 522 respectively and finally going to the first gate 524 from the second departure hall 522 which is further away from the first gate 524 compared to the first departure hall 520. The suspicious incoherent movement may be indicative, for example, of a person potentially closely exploring the airport 200B and seeking for a way to perform some illegal and/or malicious operation at the airport 200B. In another example, the suspicious incoherent movement may be indicative of an irritated and/or nervous person who is stressed due to some illegal and/or malicious operation he plans to carry out in the airport 200B. Based on this determination, the verification unit 206B1 may classify the passenger associated with the mobile wireless device 202E as a non-legitimate passenger and optionally a potential threat.

In another example, when the passenger associated with the mobile wireless device 202F arrives at the second gate 526, the verification unit 206B2 may analyze all the location certificates associated with the mobile wireless device 202F which were received from the one or more of the wireless receivers 504, specifically the wireless receivers 504 located along the path 300F. The verification unit 206B2 may extract the receiver IDs of the respective wireless receivers 504 that intercepted the device ID of the mobile wireless device 202F and transmitted respective location certificates. The verification unit 206B2 may then compute an estimated path 300F according to the predefined locations of the respective wireless receivers 504. The verification unit 206B2 may further use the timestamp included in one or more of the location certificates to compute a time-lined estimated path 300F. The verification unit 206B2 may compare the estimated path 300F to one or more approved paths leading to the second gate 526 and may determine that the estimated path 300F is highly suspicious as it starts from the personnel-only entrance 514 which is restricted to the public. The suspicious entry from the personnel-only entrance 514 may be indicative, for example, of a person trying to sneak undetected past security which is typically stationed at the main public entrances such as, for example, the first entrance 510 and/or the second entrance 512. Based on this determination, the verification unit 206B2 may classify the passenger associated with the mobile wireless device 202F as a non-legitimate passenger and optionally a potential threat.

In another example, which is very similar to the previous example, when the passenger associated with the mobile wireless device 202G arrives at the third gate 528, the verification unit 206B3 may analyze all the location certificates associated with the mobile wireless device 202G which were received from the one or more of the wireless receivers 504, specifically the wireless receivers 504 located along the path 300G. The verification unit 206B3 may extract the receiver IDs of the respective wireless receivers 504 that intercepted the device ID of the mobile wireless device 202G and transmitted respective location certificates. The verification unit 206B3 may then compute an estimated path 300G according to the predefined locations of the respective wireless receivers 504. The verification unit 206B3 may further use the timestamp included in one or more of the location certificates to compute a time-lined estimated path 300G. The verification unit 206B3 may compare the estimated path 300G to one or more approved paths leading to the third gate 528 and may determine that the estimated path 300G is highly suspicious as it starts from the emergency exit 516 which may be typically closed and restricted to the public. The suspicious entry from the emergency exit 516 may be indicative, for example, of a person trying to sneak undetected past security which is typically stationed at the main public entrances. Based on this determination, the verification unit 206B3 may classify the passenger associated with the mobile wireless device 202G as a non-legitimate passenger and optionally a potential threat.

Optionally, the verification unit 206B1 analyzes the estimated path of the with respect to one or more of the approved path(s) according to one or more deviation patterns.

For example, one or more of the passengers entering the airport 200B may travel to their designated gate through the departure halls but may deviate to some extent from the typical approved paths that serve as the basis for comparison and verification by one or more of the verification units 206, specifically the verification units 206B. For example, as seen the estimated path 300D of the passenger associated with the mobile wireless devices 202D deviates towards a first area 530 and a second area 532. However, the first and/or second areas 530 and 532 may be legitimate locations for passengers to visit, for example, toilets, a food court, a change booth, a news stand and/or the like. The verification unit 206B1 may therefore evaluate the deviation patterns identified in the estimated path 300D, specifically in the time-lined estimated path 300D to evaluate and/or determine whether the deviations are legitimate or they may be indicative of some suspicious behavior of the passenger associated with the mobile wireless devices 202D. Based on this evaluation and/or determination, the verification unit 206B1 may classify the passenger associated with the mobile wireless device 202D as a legitimate passenger or as a non-legitimate passenger and optionally a potential threat.

Optionally, one or more users associated with receptive mobile wireless devices 202 are correlated with the mobile wireless devices 202 based on visual identification of each such user in at least one image captured at a time of transmission of a location certificate from a respective one of the wireless receivers 504. At the time of the location certificate transmission, the mobile wireless devices 202 associated with the respective user is within the limited reception range of the respective wireless receiver 504 and the associated user may be therefore spatially mapped in the monitored space 200, specifically in close proximity to the respective wireless receiver 504. As such one or more images captured to depict the close proximity of the respective wireless receiver 504 at the time of the location certificate transmission may further depict the associated user. The image(s) depicting the associated user may be analyzed as known in the art to identify and extract one or more visual features of the associated user, for example, a face, a cloth article, a haircut, a body outline and/or posture and/or the like which may be used to visually correlate the respective user with its associated mobile wireless device 202.

The features of the correlated user(s) may be further detected in one or more additional images captured by one or imaging sensors deployed in the monitored space 200 and based on the identified features, the correlated user(s) may be visually tracked in the monitored space 200. Visual tracking information describing a spatial mapping (location, movement, etc.) of the correlated user(s) may be thus generated for the correlated user(s) tracked while traveling in the monitored space 200. The verification unit 206 may thus receive both the wireless mapping of one or more of the mobile wireless devices 202 and may further receive the visual tracking information of the respective associated user correlated with the respective mobile wireless device 202. The verification unit 206 may fuse together the wireless mapping information collected for a respective mobile wireless device 202 and the visual tracking information of the respective associated user visually correlated with the respective mobile wireless device 202 to compute a significantly more accurate estimated path for the respective user(s).

According to some embodiments of the present invention, the path verification may be combined for both users and disinfections apparatuses. Specifically, the path of one or more users through the monitored space 200 may be estimated and one or more (approved) paths may be defined accordingly for one or more disinfection apparatuses to follow the path(s) of the user(s) in order to disinfect surfaces which the user(s) may have touched and potentially contaminated. Moreover, the path(s) of the disinfection apparatus(s) may be verified to ensure that all surfaces suspected to be touched by the user(s) are properly disinfected.

To this end, one or more verification units 206 may be deployed in the monitored space 200 to compute an estimated path for one or more users according to the wireless mapping extracted from the location certificates collected by the mobile wireless device 202 associated with each of the user(s) from the wireless devices deployed along the respective path. One or more (approved) paths may be then predefined for one or more disinfection apparatuses based on the estimated path(s) of the user(s). In particular, the predefined path(s) may move between surfaces along the estimated path(s) of the user(s) which may have been touched and hence possibly contaminated by the user(s). The predefined path(s) may be delivered for operating the disinfection apparatus(s) accordingly to disinfect all such potentially contaminated surfaces.

During the disinfection process the mobile wireless device 202 associated with each disinfection apparatus may collect location certificates form the wireless devices located along the predefined path(s).

After completing the disinfection process according to the predefined path(s), the verification unit 206 may analyze the location certificates collected by the wireless device 202 associated with each disinfection apparatus to compute an estimated path for each disinfection apparatus and verify accordingly that the respective disinfection apparatus traveled along the predefined path to effectively carry out the disinfection process.

The descriptions of the various embodiments of the present invention have been presented for purposes of illustration, but are not intended to be exhaustive or limited to the embodiments disclosed. Many modifications and variations will be apparent to those of ordinary skill in the art without departing from the scope and spirit of the described embodiments. The terminology used herein was chosen to best explain the principles of the embodiments, the practical application or technical improvement over technologies found in the marketplace, or to enable others of ordinary skill in the art to understand the embodiments disclosed herein.

It is expected that during the life of a patent maturing from this application many relevant systems, methods and computer programs will be developed and the scope of the terms wireless transceivers and receivers and energy harvesting technologies are intended to include all such new technologies a priori.

As used herein the term "about" refers to ±10%.

The terms "comprises", "comprising", "includes", "including", "having" and their conjugates mean "including but not limited to". This term encompasses the terms "consisting of" and "consisting essentially of".

The phrase "consisting essentially of" means that the composition or method may include additional ingredients and/or steps, but only if the additional ingredients and/or steps do not materially alter the basic and novel characteristics of the claimed composition or method.

As used herein, the singular form "a", "an" and "the" include plural references unless the context clearly dictates otherwise. For example, the term "a compound" or "at least one compound" may include a plurality of compounds, including mixtures thereof.

The word "exemplary" is used herein to mean "serving as an example, an instance or an illustration". Any embodiment described as "exemplary" is not necessarily to be construed as preferred or advantageous over other embodiments and/or to exclude the incorporation of features from other embodiments.

The word "optionally" is used herein to mean "is provided in some embodiments and not provided in other embodiments". Any particular embodiment of the invention may include a plurality of "optional" features unless such features conflict.

Throughout this application, various embodiments of this invention may be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 3, 4, 5, and 6. This applies regardless of the breadth of the range.

Whenever a numerical range is indicated herein, it is meant to include any cited numeral (fractional or integral) within the indicated range. The phrases "ranging/ranges between" a first indicate number and a second indicate number and "ranging/ranges from" a first indicate number "to" a second indicate number are used herein interchangeably and are meant to include the first and second indicated numbers and all the fractional and integral numerals there between.

The word "exemplary" is used herein to mean "serving as an example, an instance or an illustration". Any embodiment described as "exemplary" is not necessarily to be construed as preferred or advantageous over other embodiments and/or to exclude the incorporation of features from other embodiments.

The word "optionally" is used herein to mean "is provided in some embodiments and not provided in other embodiments". Any particular embodiment of the invention may include a plurality of "optional" features unless such features conflict.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable sub-combination or as suitable in any other described embodiment of the invention. Certain features described in the context of various embodiments are not to be considered essential features of those embodiments, unless the embodiment is inoperative without those elements.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims.

All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention. To the extent that section headings are used, they should not be construed as necessarily limiting. In addition, any priority document(s) of this application is/are hereby incorporated herein by reference in its/their entirety.

What is claimed is:

1. A computer implemented method of verifying a path in a monitored space, comprising:
  using at least one processor of a mobile wireless device for:
    transmitting a device identification (ID) of the mobile wireless device while the mobile wireless device moves through a monitored space;

receiving at least one location certificate transmitted, in response to reception of the device ID, by at least one wireless transceiver deployed at a predefined location in the monitored space and having a limited transmission range, the at least one location certificate comprising at least the device ID and a transceiver ID of the at least one wireless transceiver;

storing the at least one location certificate; and transmitting the at least one location certificate to at least one verification unit configured to verify a path of the mobile wireless device in the monitored space estimated according to the predefined location of the at least one wireless transceiver identified by the transceiver ID extracted from the at least one location certificate;

wherein the mobile wireless device is associated with a disinfection apparatus configured to disinfect at least one surface in the monitored space, a path of the disinfection apparatus is verified with respect to at least one predefined path, the at least one wireless transceiver is deployed in association with the at least one surface.

2. The computer implemented method of claim 1, wherein the mobile wireless device is associated with a user verified based on his path through the monitored space.

3. The computer implemented method of claim 1, wherein the disinfection apparatus is configured to project Ultra Violet (UV) light to disinfect the at least one surface in the monitored space, the verification of the path of the disinfection apparatus further comprising verifying a predefined projection time of the UV light on the at least one surface which is sufficient for effectively disinfecting the at least one surface.

4. The computer implemented method of claim 1, further comprising the at least one predefined path is derived from an estimated path in the monitored space which is determined for at least one mobile device associated with a respective user such that the disinfection apparatus is verified to follow the path of the respective user.

5. The computer implemented method of claim 1, wherein the estimated path is verified based on comparison with at least one approved path.

6. The computer implemented method of claim 1, wherein the limited transmission range defines a limited space in the monitored space in proximity to the at least one wireless transceiver such that only when located within the limited space the mobile wireless device receives the at least one location certificate transmitted by the at least one wireless transceiver.

7. The computer implemented method of claim 1, wherein the device ID is transmitted periodically and/or continuously.

8. The computer implemented method of claim 1, further comprising the at least one location certificate is encrypted using at least one cryptographic key available to the at least one wireless transceiver and to the at least one verification unit.

9. The computer implemented method of claim 1, wherein the at least one location certificate further comprises a timestamp indicative of a transmission time of the at least one location certificate, the at least one verification unit uses the timestamp to timeline the estimated path.

10. The computer implemented method of claim 1, further comprising the at least one wireless transceiver transmits at least one additional location certificate in case the mobile wireless device exits and re-enters the limited transmission range of the at least one wireless transceiver.

11. The computer implemented method of claim 1, wherein the at least one wireless transceiver is a battery-less wireless transceiver powered by energy harvested from the transmission of the mobile wireless device.

12. A mobile wireless device for verifying a path in a monitored space, comprising:

at least one processor executing a code, the code comprising:

code instructions to transmit a device identification (ID) of the mobile wireless device while the mobile wireless device moves through a monitored space;

code instructions to receive at least one location certificate transmitted, in response to reception of the device ID, by at least one wireless transceiver deployed at a predefined location in the monitored space and having a limited transmission range, the at least one location certificate comprising at least the device ID and a transceiver ID of the at least one wireless transceiver;

code instructions to store the at least one location certificate; and code instructions to transmit the at least one location certificate to at least one verification unit configured to verify a path of the mobile wireless device in the monitored space estimated according to the predefined location of the at least one wireless transceiver identified by the transceiver ID extracted from the at least one location certificate;

wherein the mobile wireless device is associated with a disinfection apparatus configured to disinfect at least one surface in the monitored space, a path of the disinfection apparatus is verified with respect to at least one predefined path, the at least one wireless transceiver is deployed in association with the at least one surface.

13. A computer implemented method of verifying a path in a monitored space, comprising:

using at least one processor for:

receiving at least one location certificate from at least one wireless receiver deployed at a predefined location in the monitored space and having a limited reception range, the at least one location certificate comprising at least a device identification (ID) of a mobile wireless device detected by the at least one wireless receiver and a receiver ID of the at least one wireless receiver;

extracting the device ID and the receiver ID from the at least one location certificate;

estimating a path of the mobile wireless device in the monitored space according to the predefined location of the at least one wireless receiver identified by the receiver ID; and verifying the estimated path based on comparison with at least one approved path;

wherein the at least one wireless receiver is of a mobile wireless device which is associated with a disinfection apparatus configured to disinfect at least one surface in the monitored space, a path of the disinfection apparatus is verified with respect to at least one predefined path, the at least one wireless transceiver is deployed in association with the at least one surface.

14. The computer implemented method of claim 13, wherein the limited reception range defines a limited space in the monitored space in proximity to the at least one wireless receiver such that only when located within the limited space the at least one wireless receiver receives the device ID transmitted by the mobile wireless device.

15. The computer implemented method of claim 13, further comprising estimating a timeline of the path according to a timestamp extracted from the at least one location certificate.

16. The computer implemented method of claim 13, further comprising the at least one wireless receiver transmits at least one additional location certificate in case the mobile wireless device exits and re-enters the limited reception range of the at least one wireless receiver.

17. The computer implemented method of claim 13, wherein the mobile wireless device is associated with a user verified based on his path through the monitored space.

18. The computer implemented method of claim 17, further comprising correlating between the mobile wireless device and the associated user based on analysis of at least one image captured at a time of transmission of the location certificate by at least one imaging sensor configured to monitor the predefined location of the at least one wireless receiver.

19. The computer implemented method of claim 18, further comprising estimating the path of the associated user through the monitored space based on detection of the associated user in at least one image captured by at least one imaging sensor deployed in the monitored space.

20. A system for verifying a path in a monitored space, comprising:
- at least one processor executing a code, the code comprising:
  - code instructions to receive at least one location certificate from at least one wireless receiver deployed at a predefined location in the monitored space and having a limited reception range, the at least one location certificate comprising at least a device identification (ID) of a mobile wireless device detected by the at least one wireless receiver and a receiver ID of the at least one wireless receiver;
  - code instructions to extract the device ID and the receiver ID from the at least one location certificate;
  - code instructions to estimate a path of the mobile wireless device in the monitored space according to the predefined location of the at least one wireless receiver identified by the receiver ID; and
  - code instructions to verify the estimated path based on comparison with at least one approved path;
  - wherein the at least one wireless receiver is of a mobile wireless device which is associated with a disinfection apparatus configured to disinfect at least one surface in the monitored space, a path of the disinfection apparatus is verified with respect to at least one predefined path, the at least one wireless transceiver is deployed in association with the at least one surface.

* * * * *